(12) United States Patent
Nickel et al.

(10) Patent No.: US 8,637,233 B2
(45) Date of Patent: Jan. 28, 2014

(54) DEVICE AND METHOD FOR IDENTIFYING MICROBES AND COUNTING MICROBES AND DETERMINING ANTIMICROBIAL SENSITIVITY

(75) Inventors: Cynthia S. Nickel, Wimberley, TX (US); Clois E. Powell, Seguin, TX (US); James R. Biard, Richardson, TX (US); William A. Stapleton, San Marcos, TX (US); Gary M. Aron, San Marcos, TX (US); Jeanette Hill, Manor, TX (US); Ray G. Cook, San Marcos, TX (US); Daniel M. Justiss, Austin, TX (US); Frederick J. Strieter, Dallas, TX (US); Wayne T. Kilian, Telephone, TX (US); Andrei M. Manoliu, Atherton, CA (US)

(73) Assignees: Telemedicine Up Close, Inc., Frisco, TX (US); Texas State University, San Marcos, TX (US)

( * ) Notice: Subject to any disclaimer, the term of this patent is extended or adjusted under 35 U.S.C. 154(b) by 0 days.

(21) Appl. No.: 13/464,936

(22) Filed: May 4, 2012

(65) Prior Publication Data
US 2013/0017534 A1    Jan. 17, 2013

Related U.S. Application Data

(60) Provisional application No. 61/482,569, filed on May 4, 2011, provisional application No. 61/493,152, filed on Jun. 3, 2011.

(51) Int. Cl.
*C12Q 1/00* (2006.01)
(52) U.S. Cl.
USPC .............................................................. 435/4
(58) Field of Classification Search
None
See application file for complete search history.

(56) References Cited

U.S. PATENT DOCUMENTS

| 5,282,940 | A  | * | 2/1994  | Griffis et al. ................. 426/237 |
| 6,669,928 | B1 | * | 12/2003 | Gurol ............................. 424/49 |
| 7,229,754 | B2 |   | 6/2007  | Kish et al. |
| 2005/0048599 | A1 |   | 3/2005  | Goldberg et al. |
| 2006/0115824 | A1 |   | 6/2006  | Samadpour |
| 2011/0201739 | A1 |   | 8/2011  | Beall |

FOREIGN PATENT DOCUMENTS

WO    2010093861 A2    8/2010

OTHER PUBLICATIONS

International Search Report from PCT/US2012/036689, dated Nov. 30, 2012, 2 pgs.
"Performance Standards for Antimicrobial Susceptibility Testing; Twenty-Second Information Supplement", Jan. 2012, vol. 32 No. 3.
"Performance Standards for Antimicrobial Disk Susceptibility Tests; Approved Standard-Eleventh Edition", Jan. 2012, vol. 32 No. 1.

* cited by examiner

*Primary Examiner* — Albert Navarro
(74) *Attorney, Agent, or Firm* — Abel Law Group, LLP

(57) ABSTRACT

A method of determining antimicrobial activity of an agent can include providing a well, wherein the well contains at least one antimicrobial agent, the well further including at least two electrodes. A sample of a microbe can be added into the well and a voltage pulsed between the electrodes. An electrical property can be sampled and recorded. In another aspect, a method of identifying at least one microbe includes taking a sample containing the at least one microbe, isolating the at least one microbe from the sample, dividing the at least one microbe into a at least one well, wherein each well contains at least one antimicrobial agent and at least two electrodes. A voltage is pulsed between the at least two electrodes, an electrical property is sampled during the pulsing and recorded. In another aspect, a diagnostic device for detecting at least one microbe is presented.

11 Claims, 17 Drawing Sheets

DEVICE AND METHOD FOR IDENTIFYING MICROBES AND COUNTING MICROBES AND DETERMINING ANTIMICROBIAL SENSITIVITY

CROSS-REFERENCE TO RELATED APPLICATION(S)

The present application claims priority from U.S. Provisional Patent Applications No. 61/482,569, filed May 4, 2011 and 61/493,152, filed Jun. 3, 2011 both entitled "DEVICE AND METHOD FOR IDENTIFYING MICROBES AND COUNTING MICROBES AND DETERMINING ANTIMICROBIAL SENSITIVITY," both naming inventors Cynthia Nickel et al., which both applications are incorporated by reference herein in its entirety.

FIELD OF THE DISCLOSURE

The disclosure, in general, relates to microbial diagnostics applicable to the fields of human health care, animal medicine, animal care, clinical laboratories, biomedical and biological research, food control, and all industries impacted by microbes.

BACKGROUND

In 1942, for the first time, the life of a patient was saved by treatment with penicillin. Yet, the battle against infectious diseases and pathogenic bacteria continues. In 2006, the Infectious Disease Society of America reported that each year, 90,000 of the 2 million people who acquire a hospital bacterial infection will die. That is a 4.5% mortality rate resulting from just visiting a hospital. Multi-drug resistance bacterial strains are a major problem and one that has been increasing very rapidly every year during the last few decades. Beside the need for new antibiotics, there is also a need to quickly identify and quantify a bacterial infection in order to embank the spread of the infection into an epidemic.

In the food industry, pasteurization involves heating liquid food products like milk, juices, etc. to kill pathogenic organisms such as viruses, bacteria, molds, and yeast. However, some amount of microbes may survive the pasteurization process or may be inadvertently introduced during further processing. Such microbes typically cause spoilage of food products causing an economic loss exceeding $1 billion each year. Moreover, if the surviving microbes are pathogenic, outbreaks of food borne illnesses may occur among consumers. It has been estimated that approximately 76 million food borne illnesses occur per year in the U.S. alone, of which up to 5000 cases result in death, thereby affecting the economic loss even further.

Therefore, detecting and quantifying microbes that survive treatments such as pasteurization is important for assuring food quality and food safety and further for complying with standards set by government agencies or trade organizations. For example, the U.S. Pasteurized Milk Ordinance requires that "Grade A" pasteurized milk has a total microbial count of not more than 20,000 colony forming unit (CFU)/ml and a coliform count of not more than 10 CFU/ml. Food producers and/or market food distributors have to perform microbiological tests to fulfill the regulatory standards. It is important to their economic operation that they do so with the least possible expenditure of material and labor.

There are presently several ways to detect microbes in clinical or food samples. Broadly categorized, there are (i) traditional methods such as plate cultures and biochemical assays, (ii) DNA and antibody based methods, often involving micro/nano particles and fluorescence, and (iii) other "automated" techniques that rely on monitoring the effects of bacterial metabolism on the medium. Of these, traditional methods are the most extensively used, and often serve as the standard to which other techniques are compared. However, such traditional methods are tedious, labor intensive, and require very long times to detect microbes, which can range from overnight to weeks depending on the type of the organism and medium used.

The foregoing are solely two examples how microbes affect people's daily life and the economy. It is well known how widespread the impact of such microbes is, spanning from the health care and pharmaceutical sectors, over the food and livestock sectors, into municipal and rural population, even into the oil and gas industries, and industries served with pipelines or storage tanks are corroded by microorganisms present. Therefore, in a broad area of economic fields, there is a need to provide an improved method and device to detect, identify, quantify, viable microbes in a sample.

SUMMARY OF THE INVENTION

In one aspect, a method for monitoring the viability of microbes includes placing a sample of the microbes in a well, the well is configured with at least two electrodes. A voltage is pulsed between the two electrodes and an electrical property is sampled during the voltage pulse. The electrical property is recorded as a function of time and analyzed to determine microbial growth.

In another aspect, a method for identifying bacteria includes taking a sample of the bacteria, isolating the bacteria from the sample and dividing the bacteria into a number of wells, wherein each well is configured with two electrodes. The method further comprises adding bacteriophages specific to the bacteria being identified to at least one of the wells. A voltage is pulsed between the two electrodes and an electrical property is sampled during the voltage pulse. The electrical property is recorded as a function of time and analyzed looking for a distinct digital signature of a successful bacteriophage attack.

In another aspect, a method for determining the count of microbes in a sample includes filtering the sample to separate the microbes from the sample, and immersing the microbes in a life supporting medium (henceforth called analyte) to form an immersion. The immersion is divided into wells, and a voltage is pulsed between the two electrodes and an electrical property is sampled during the voltage pulse. The electrical property is recorded as a function of time and analyzed. The electrical property is correlated to a count.

In one other aspect, a method for determining antimicrobial resistance of microbes, includes adding a sample of microbes into a well containing at least one antimicrobial, and measuring the viability or growth rate of the microbes by placing a sample of the microbes in a well, the well is configured with at least two electrodes. A voltage is pulsed between the two electrodes and an electrical property is sampled during the voltage pulse. The electrical property is recorded as a function of time and analyzed to determine microbial reaction to the antimicrobial.

In yet another aspect, a diagnostic device for detecting viability of microbes includes a set of stackable units. The first unit is a diagnostic unit having a series of wells. The wells have electrodes contacting the inside and the outside of the wells. The first unit also has a connection mechanism to facilitate control of the automated sample preparation. The second unit is a reader unit. The reader unit includes a connector section for the electrodes and the automated sample preparation.

In even another aspect, a diagnostic device for identifying microbes in a sample, includes a first unit and a second unit, wherein the first unit is stackable into the second unit. The first unit is a diagnostic unit including wells, the wells having electrodes contacting the inside and the outside of the well. The first unit also has a connection mechanism to facilitate control of the automated sample preparation. The diagnostic unit also includes bacteriophage. The second unit is a reader unit and includes a connector section for the electrodes of the diagnostic unit and the automated sample preparation.

In one further aspect, a diagnostic device for determining the count of microbes in a sample includes a first unit and a second unit, wherein the first unit is stackable into the second unit. The first unit is a diagnostic unit including wells, the wells having electrodes contacting the inside and the outside of the well. The first unit also has a connection mechanism to facilitate control of the automated sample preparation. The second unit is a reader unit and includes a connector section for the electrodes of the diagnostic unit and the automated sample preparation, and the reader unit includes a memory chip containing correlation data.

In another aspect, a diagnostic device for determining antimicrobial resistance microbes in a sample includes a first unit and a second unit; the first unit is stackable into the second unit. The first unit is a diagnostic unit including wells, the wells having electrodes contacting the inside and the outside of each well and an automated sample preparation system. The diagnostic unit also includes antimicrobials. The second unit is a reader unit and includes a connector section for the electrodes of the diagnostic unit and mechanisms for driving the first unit's automated sample preparation system.

BRIEF DESCRIPTION OF THE DRAWINGS

So that the manner in which the features and advantages of the embodiments are attained and can be understood in more detail, a more particular description of the embodiments briefly summarized above may be had by reference to the appended drawings. However, the drawings illustrate only some embodiments and therefore are not to be considered limiting of the scope of the invention which may admit to other equally effective embodiments.

DETAILED DESCRIPTION OF THE INVENTION

Figure 1:
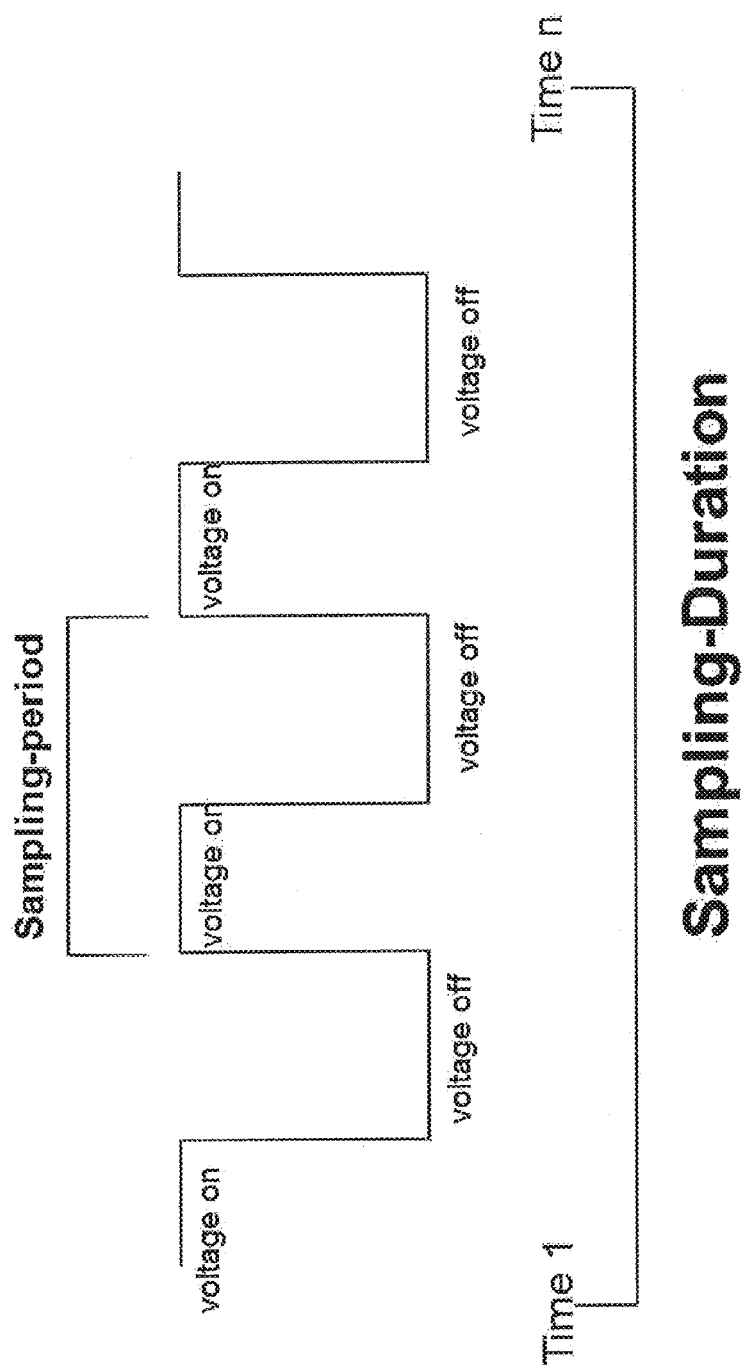
FIG. 1 includes a plot of voltages pulses. Further support for voltage pulse selection is found in FIG. 9.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

The metabolism of microbes in a medium results in the release of electrolytes such as carbonates, organic acids, and salts of sodium, potassium and magnesium into the biomass, i.e., as a colony of microbes is growing, the electrolytes are being exchanged with the medium and certain life-events change the electrolytes in a predictable fashion. For example when bacteriophages attack a bacterium, up to $10^8$ potassium ions are released.

On a molecular level, conductance in a medium is a direct result of mobility of molecules and microbes can be viewed as a complex of molecules and impacts conductance accordingly. As the colony of microbes grow, the conductance increases in a predictable fashion according to Ohm's Law and making use of equivalent-conductance relations (law of Kohlrausch) and the Debye-Hueckel theory. As a consequence of life events of the microbes, the electric property of the medium changes similar to conductometric titrations.

The principle for detection relies on the easily quantifiable and measurable change in electrical properties as a function of ion content. For example, conductometric titration is a well-established example of the utility of the method. Ion conductivity in water is a function of ion mobility in water. For example, examination of ions produced from the metals from the first column in the Periodic Table indicate that lithium is the smallest ion, sodium next larger in size, potassium even larger, etc. However, lithium ion has the lowest conductivity of all the metal ions found in the first column of the Periodic Table. This is because lithium ion is very hydrophilic and builds a large water of hydration structure around it. The conductive response of these ions is very specific and, as a consequence, their concentrations (and changes in concentration) are easily measured. As the change in concentration of the potassium ions increase with a specific phage attack of specific harmful microbes, the change in concentration of potassium ion can easily be measured by changes in conductivity and conversely resistance and capacitance of the solution. Therefore, as a result, if one would monitor the change of electrical properties of a growing colony of microbes over time, one would observe a decrease of resistance component of total impedance. This change of an observable electrical property, here resistance and capacitance, over time forms a signature which individually or together have characteristics attributable to the concentration or count of the microbes. When some or all of the electrical properties are used, various life signs of bacteria may be detected.

Furthermore, if a colony has reached its maximum growth and stagnate in its population, the signature would indicate no change in the electrical property. Taking this concept further, if a colony begins to decline in population, their bodies decay into electrically inert pieces and do not participate in the conductivity of the medium and the resistance in the medium increases and can conclude the colony is dying.

This concept provides the basis for a method that identifies viability of a microbial colony, providing a positive signature for a growing colony because the resistance part of impedance is decreasing over time, a constant signature for a stagnating population because the resistance part of impedance is constant and a negative signature for a depleting colony because the resistance part of impedance is increasing.

The concept can be even further refined if one applies agents that target specific microbial species. For example, if one adds an antimicrobial to the medium and the antimicrobial is active against the growing colony, the result would be an observation of a negative signature, or for slow acting antimicrobials a constant signature for a stagnating population. Likewise, the addition of an inactive antimicrobial to the medium would result in a signature representing continued growth of the colony. Furthermore, slight changes in the signature, would give information as to the sensitivity of the microbes towards the applied antimicrobial.

Moreover, the concept can be even tuned to identifying one specific species of bacteria by applying bacteriophages or phages (also considered to be an antimicrobial). Phages are viruses that infect and kill bacteria. Generally, phages are lytic and cause lysis of the bacteria resulting in a distinctive signature. Furthermore, the vast number of phages available allow for methods to identify a single species of bacteria, a class of bacteria, or even a mixture of bacteria.

When phages attack a bacteria $10^8$ potassium ions are released into the medium decreasing the resistance part of total impedance momentarily until the bacteria then reabsorb the ions during their recovery cycle. The change in resistance of the medium is immediate and the recovery occurs across a five minute time span. So without waiting for the bacteria to lysis, the phage attack can be determined.

The viability of microbes in a medium can be measured by monitoring changes in the electrical properties in the medium. Change of an electrical property over time is defined as a signature. Electrical properties can be measured by at least two electrodes present in a well, such as a sample well, containing the microbes in a supportive medium, such as LB broth.

Measuring the electrical property should be done in such a way that the microbes in the aqueous medium are not or minimally affected by voltages or currents applied to the sample well. One way to minimize this is by a procedure called sampling.

1. Sampling

FIG. 1 depicts the concept of sampling. A voltage is pulsed between two electrodes in the well containing a microbe sample in a supportive medium. The voltage pulse comprises an on-period and an off-period. The sampling-period is defined by the total length of time that voltage is applied plus the time that the voltage is removed, i.e., the on-period+the off-period.

In embodiments, the measuring circuit comprises a sample cell containing the microbes in a supportive growth medium of LB Broth, at least two electrodes for applying a voltage and measuring conductance. A constant voltage, or reference voltage is applied to one electrode and the other electrode is connected to a source of DC voltage that is applied at intervals to create a current measuring circuit capable of measuring total impedance including resistance and conductance. The current measuring circuit includes a low-noise amplifier with a feedback resister; the reference voltage can be 0.0V or any other DC voltage that is suitable for ease of implementation of the low-noise amplifier. Then DC voltage is applied to the other electrode using a circuit with a low-noise amplifier and as the voltage is applied, the current is measured according to the clock device. In some cases, it is advantageous for the voltage applied to each current measuring circuit to have opposite polarity from one sampling-period to the next.

In some embodiments, it can be advantageous to measure resistance, capacitance, and inductance, or total impedance, for which an alternating current (AC) can be applied during the sampling-period instead of a direct current (DC).

In other embodiments, a thermistor or similar device can be added to the measuring circuit used to capture temperature during the sampling-period. In yet other embodiments, a pH electrode or pH probe can be added to the circuit to capture pH and changes of the pH during the sampling.

In embodiments, the applied on-period of voltage is at least about 1 millisecond, at least about 2 milliseconds, at least about 3 milliseconds, at least about 5 milliseconds, at least about 10 milliseconds, at least about 15 milliseconds, at least about 20 milliseconds, at least about 50 milliseconds, at least about 100 milliseconds, at least about 200 milliseconds, or at least about 500 milliseconds.

In other embodiments, the on-period is not greater than about 500 milliseconds, not greater than about 200 milliseconds, not greater than about 100 milliseconds, not greater than about 50 milliseconds, not greater than about 20 milliseconds, not greater than about 10 milliseconds, not greater than about 5 milliseconds In other embodiments, the off-period is at least about 100 milliseconds, at least about 200 milliseconds, at least about 500 milliseconds, at least about 1 second, at least about 2 seconds, at least about 3 seconds, at least about 5 seconds, at least about 10 seconds, at least about 20 seconds, at least about 40 seconds, or at least about 50 seconds, or at least about 1 minute.

In yet other embodiments, the off-period is not greater than about 60 seconds, not greater than about 30 seconds, not greater than about 10 seconds, not greater than about 5 seconds, not greater than about 2 seconds, not greater than about 1 second, not greater than about 500 milliseconds, not greater than about 200 milliseconds, not greater than about 100 milliseconds, or not greater than about 50 milliseconds.

In yet other embodiments, the sum of on period is between one second and one minute. For example, the on-period can be 50 milliseconds and the off-period can be 950 milliseconds. In other examples, the on-period can be 5 milliseconds and the off-period can be 995 milliseconds. From these examples, it can be seen that the on-period comprises a relative short fraction of the sampling period, while the off-period comprises the majority of the sampling period. Accordingly, during the monitoring, the sample is exposed to a voltage and current only for a brief duration.

In embodiments, the voltage applied to a sample is DC voltage can be at least about 0.0005 V, at least about 0.001 V, at least about 0.002 V, at least about 0.005 V, at least about 0.01 V, at least about 0.02 V, at least about 0.05 V, at least about 0.1 V, at least about 0.2 V, 5 V, at least about 1.0 V, at least about 2.00 V, at least about 5.0 V, or at least about 10.0 V.

In yet other embodiments, the voltage is not greater than about 5.0 V, not greater than about 2.0 V, not greater than about 1.0 V, not greater than about 0.5 V, not greater than about 0.2 V, or not greater than about 0.1 V. For example, the voltage can be applied between 50 mV to 1.24 volts and still be below the electrolysis of water or other ingredients of the sample well.

In embodiments, the sampling-duration is defined by the total number of sampling-periods. The sampling-duration varies by the diagnostic function being implemented. For example, bacterial identification's sampling-duration can be from 2 minutes to 10 minutes. Yet in other embodiments, the sampling duration can be from 2 minutes to 30 minutes, or even 60 minutes. In another example, antimicrobial sensitivity test sampling-duration can be from 40 minutes to 4 hours. Yet in other embodiments, the antimicrobial sensitivity test sampling can be longer than 4 hours. In yet another example, the colony counter can have a sampling duration of one sampling-period. Thus, the colony counting can be achieved in as little as one minute.

In embodiments, testing or monitoring the viability of microbes can take not longer than about 360 minutes, not longer than about 180 minutes, not longer than about 120 minutes, or not longer than about 90 minutes. In yet other embodiments, testing or monitoring the viability of microbes can take not longer than about 60 minutes, not longer than about 45 minutes, or not longer than about 30 minutes. In even further embodiments, testing or monitoring viability of microbes can take not longer than about 20 minutes, not longer than about 10 minutes, not longer than about 5 minutes, or not longer than about 2 minutes.

The method according to any one of the preceding claims, wherein the monitoring of the viability is between about 15 seconds and about 60 minutes, between about 15 seconds and about 45 minutes, between about 15 seconds and about 20 minutes, between about 15 seconds and about 10 minutes, between about 1 minute and about 20 minutes, between about 2 minutes and about 20 minutes, between about 5 minutes and about 20 minutes, between about 5 minutes and about 10 minutes, or between about 10 minutes and about 20 minutes.

Figure 9A:
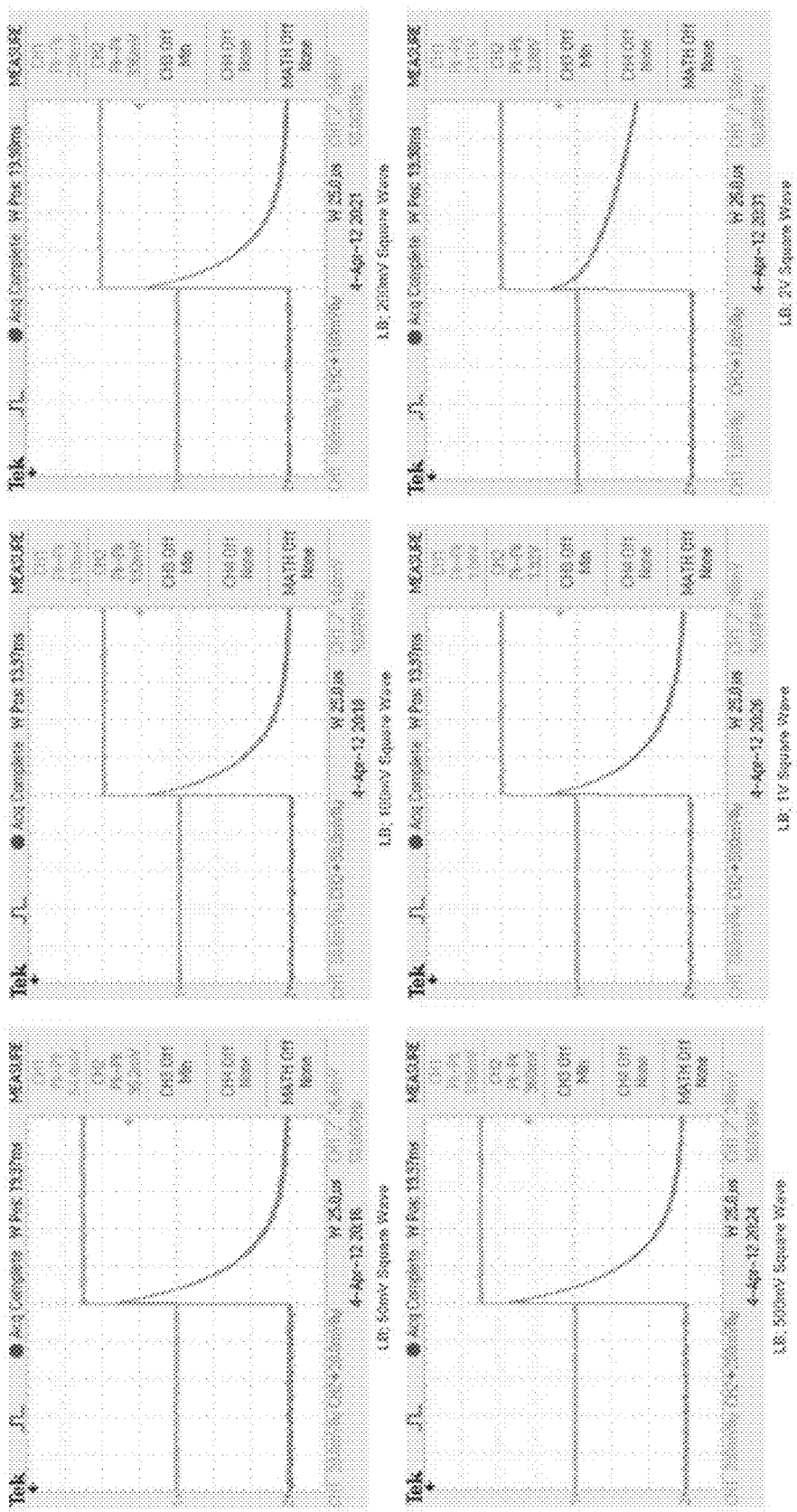
FIG. 9 include a method for determining the correct voltage, pulse length, and sampling given a particular analyte FIG. 10 include an illustration of a multiplexed sensor with a 4×4 sensor configuration as an extension of FIG. 8c.
Figure 9B:
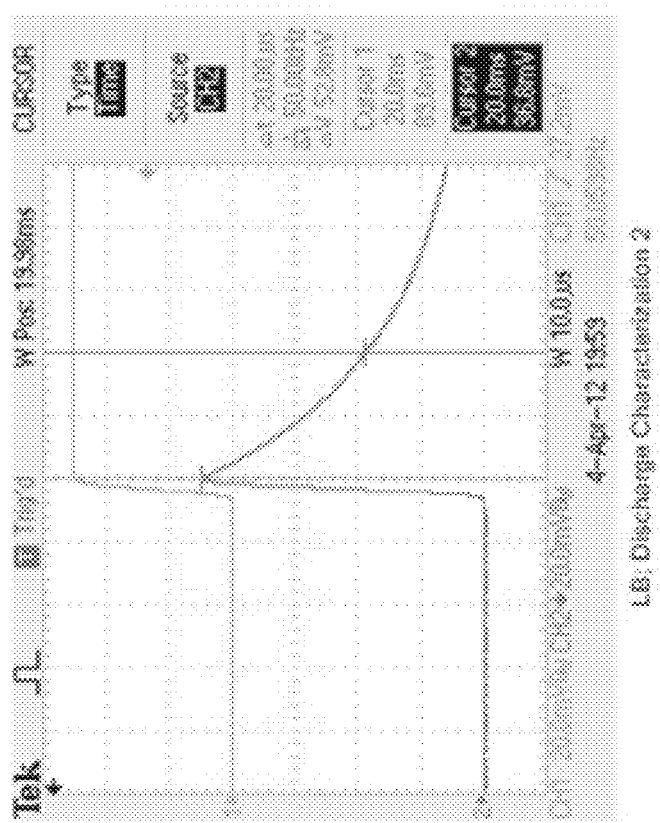
Figure 9B:
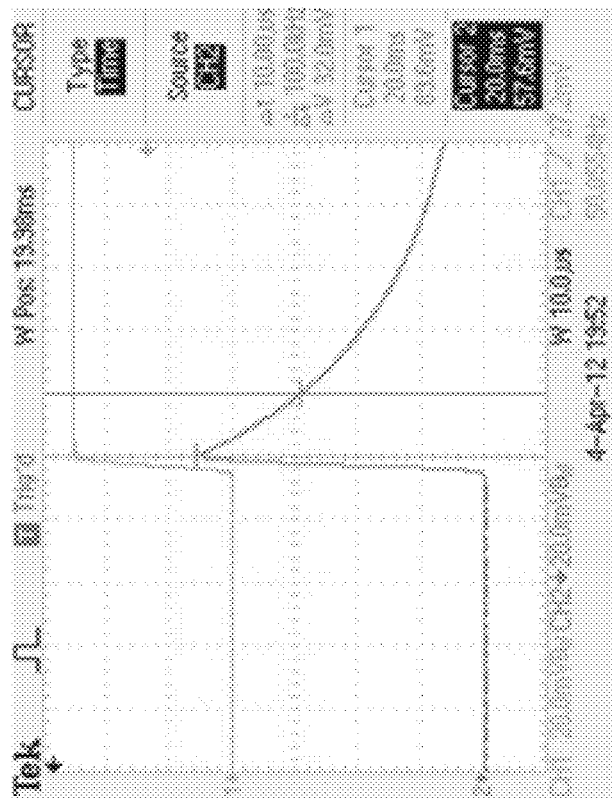
Figure 10A:
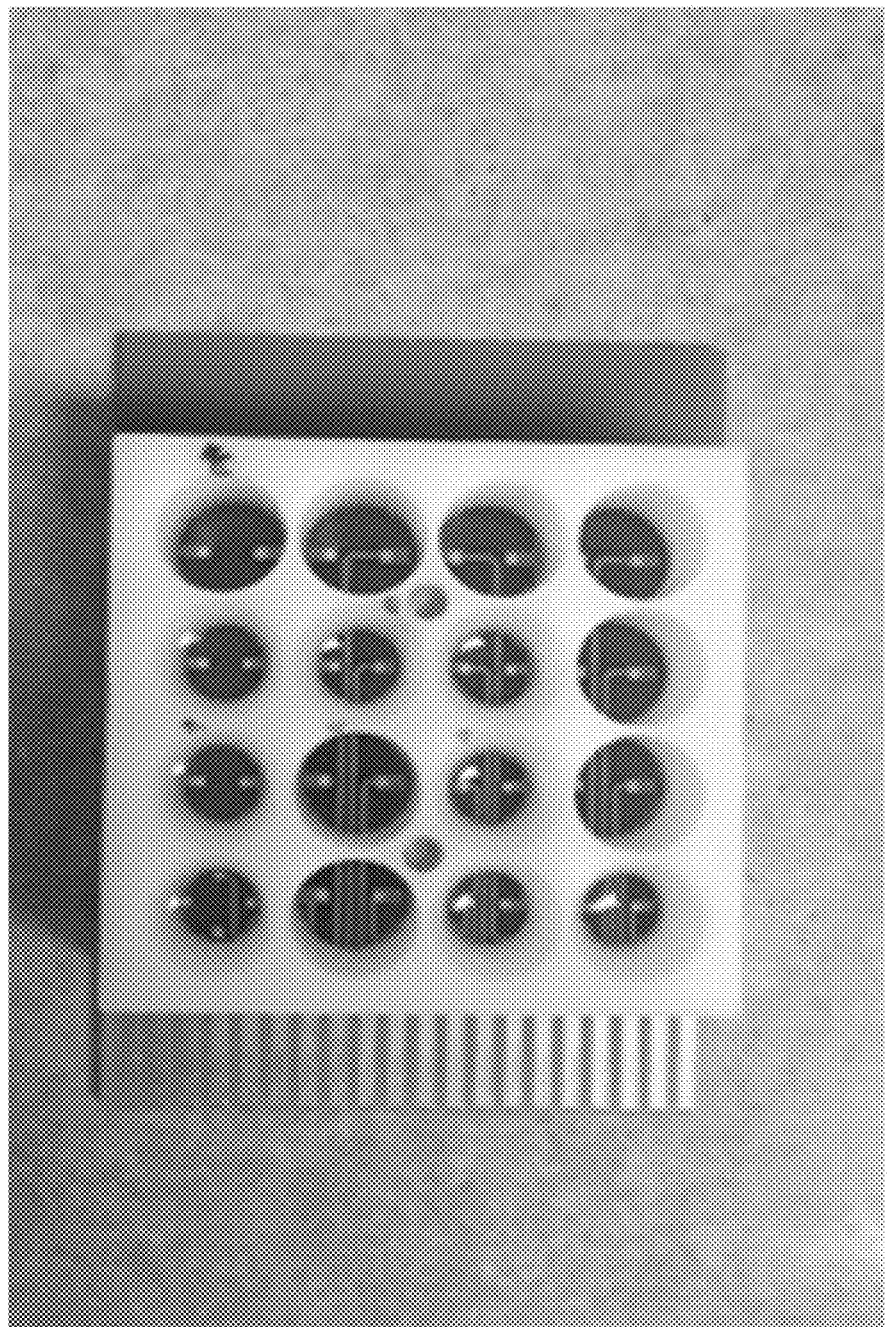
Figure 10B:
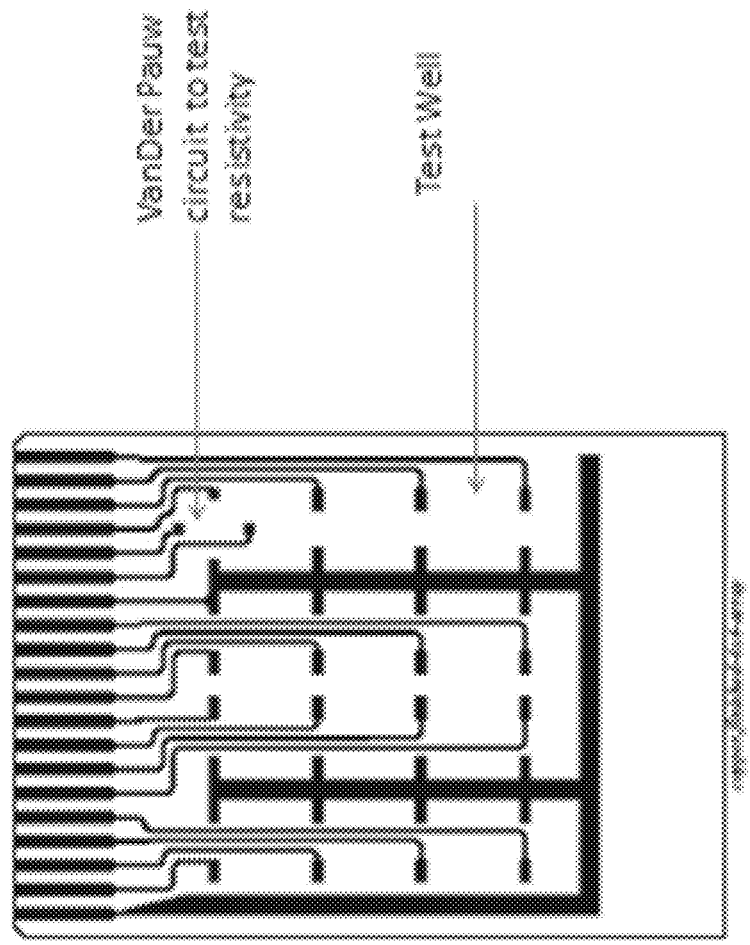

Refinement of Signal Fidelity (FIGS. 9a-9b) and (FIG. 10)

In order to improve fidelity of the signal for a particular analyte, multiple electrical properties may be sampled, and the voltage strength and pulse on and pulse off-period must be carefully tuned to the analyte. In one embodiment of the invention resistance, capacitance and the electrical time constant was sampled and the system can be characterized by a RC circuit model.

In this embodiment, circuitry was constructed to provide a low impedance voltage buffer to drive the cell under test, with a transimpedance amplifier to convert the resulting cell current into a voltage signal. This allowed characterization of the cell response to proceed with a good signal-to-noise ratio and high repeatability. A signal generator was used that output a positive pulse at several pulse amplitudes to refine the signal generation and sampling.

The 4×4 test cells, FIG. 10a, that were tested under the above conditions with LB broth show an ionic solution about resistance of 550 OHMs and an electrode capacitance of 0.04 uF. With a 50 mV positive pulse, the initial test cell current (peak) is +91 uA. This current produces a peak transimpedance amplifier output voltage of −91 mV. During the positive voltage pulse the test cell current decreases exponentially as the electrode capacitance charges. This exponential current trace has time constant of 22 us.

Verification that the cell responds as a linear network, at low signal levels, and measurement of the resistance and capacitance that comprise this equivalent series RC circuit, provided a foundation for comparing different analytes. At higher signal levels nonlinear effects take over as the system loses scaling and time invariance, making comparisons more difficult. Operating well into the nonlinear regime can cause permanent changes in the response, often with visible signs of electrode corrosion.

An important part of this work was identifying the boundary separating the linear and nonlinear regimes. To remain below the threshold of departure from the linear model, maximum test signal amplitudes should be characterized for the analyte solution and operating below the threshold is required.

4×4 Sensor (FIG. 10)

One embodiment of the sensor was made by placing copper traces on a circuit board, then using solder mask to provide at least two electrodes of diameter 1 mm with centers 5 mm apart in each cell. A standard electroless nickel-gold plating process was then used to coat the traces with gold. The gold thickness in the IPC-4552, Specification for Electroless Nickel/Immersion Gold (ENIG) Plating for Printed Circuit Boards is 1.97 microinches minimum. The nickel thickness is 118.1 to 236.2 microinches thick. A solder mask was carefully applied leaving two circular electrode patterns exposed and carefully spaced at the appropriate area in each cell. It is important to size the ending square pads of each electrode so they are large enough to accommodate the inaccuracy of solder mask application. The functioning of the sensor is dependent on the relationship of the diameter of the opening in the solder mask, the distance between the openings and the size of the cell holding the solution. In this embodiment, sixteen 1 cm diameter holes were bored in a Delrin block. Then the Delrin block was attached to the circuit board using an epoxy adhesive. In this embodiment each cell holds approximately 1 ml of liquid. In this embodiment a Van Der Pauw cell was added to aid in process control during manufacturing.

Other embodiments can be made using injection mold techniques using a wiring harness.

Another embodiment could coat the copper traces on the circuit board or wires in the wiring harness with graphene or other conductive materials instead of gold.

2. Diagnostic System

Figure 2:
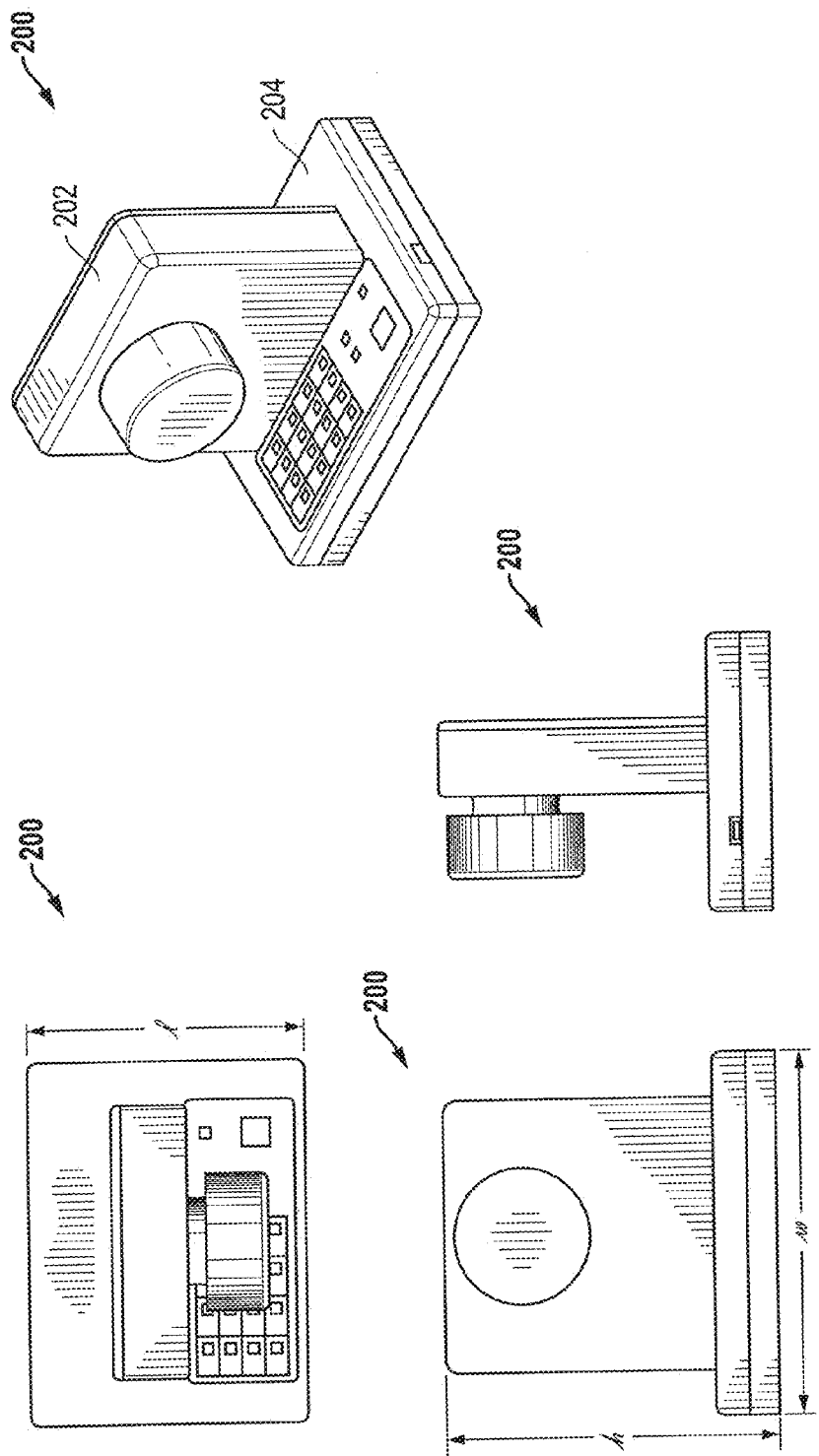
FIG. 2 includes an illustration of an embodiment of a diagnostic device.

FIG. 2 displays an implementation of the diagnostic system 200 in its assembled configuration and this configuration is optimized for testing of liquid samples, such as urine. The diagnostic system comprises two stackable units, the diagnostic unit 202 and the reader unit 204. The diagnostic system 200 has an outside length l, width w, and height h in its stacked configuration. The length can be between about 2.5 and about 4.5 inches, preferably, between about 3.0 and about 4.0 inches, more preferably about 3.5 inches. The width w of the reader unit 204 and can range from about 3.5 to about 5.5 inches, preferable between about 4.0 and about 5.0 inches, more preferably, about 4.4 inches. The heights h is depending from the size of the diagnostic unit 202 and can range from about 3.5 to about 5.0 inches, preferable between about 4.0 and about 4.5 inches, more preferably, about 4.2 inches. In other embodiments, the stackable units can stack in a side by side configuration. In other embodiments, the stackable units can be miniaturized to accommodate lessor volumes required when testing other sample types. In other embodiments, the stackable units can be formed into one integrated unit.

Figure 3:
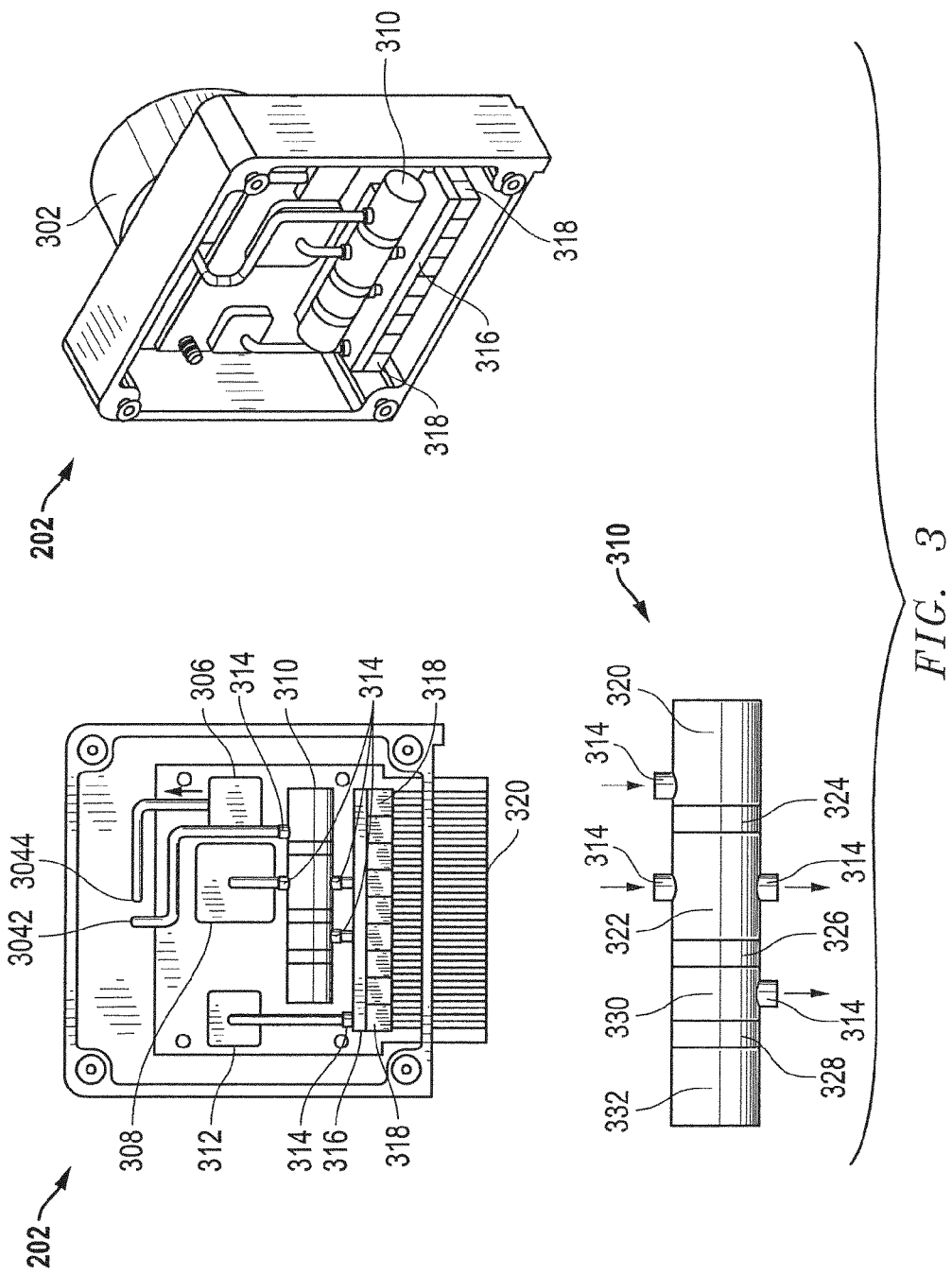
FIG. 3 includes an illustration of an embodiment of the diagnostic unit of the diagnostic device.

FIG. 3 depicts the interior of the diagnostic unit 202. The interior of the diagnostic unit has an assembly of tubes, liquid compartments, filters, and wells. The flows of a sample and other liquids can be regulated by pressure applied in series to chambers 312, 306, 308. Valves 314 can be one-way valves, i.e., allowing flow only in one direction. The valves can control flows into and from 320, 322, 330, and into 332, and also into and from manifold 316 and further into wells 318. In other embodiments, pressure can be independently regulated by an electronic mechanism present in reader unit 204 and further discussed below.

A sample holder 302 receives a sample from a patient. The samples can be taken from urine, blood, sweat, mucus, saliva, semen, vaginal secretion, vomit, tears, sebum, pleural fluid, peritoneal fluid, gastric juice, earwax, cerebrospinal fluid, breast milk, endolymph, perilymph, aqueous humor, vitreous figured in such way that a positive pressure is created inside the sample holder during the tightening of the cap.

Some embodiments can have the reader unit 204 provide pressure to the fluidic system of the diagnostic unit using an electronic pressurizing system instead of the screw cap pressure system. The reader unit's pressurizing system would then connect to the diagnostic unit via at least one pressure port.

While the sample remains in sample holder 302, pressure forces liquid from chamber 312 into the manifold 316 and then evenly into wells 318. Antimicrobial or bacteriophage can be stored dry separately in some or all wells. Liquid that flows into wells 318 dissolve or emulsify these antimicrobials or bacteriophages. The liquid will depend on best practices for dissolving the antimicrobials or bacteriophages. Some embodiments will have more than one chamber such as chamber 312. For example, when different dried materials require different liquids for reconstituting, dissolving, or preparing antimicrobials or bacteriophages, additional chambers such as chamber 312 will hold the necessary liquid. Some embodiments divide each chamber 318 into two halves and the dissolved or emulsified antimicrobial flow into one half then through a micron filter and one-way valve into the other half. Some of the wells receive the microbial sample after the sample has been filtered and prepared. The volume of this liquid can range between 4.0 ml to 12 ml depending on donor sample type.

3044 displays a tube that connects liquid compartment 306 with the sample holder 302. Liquid compartment 306 can contain an aqueous liquid, deionized water, buffer, or broth. The liquid in 306 can serve various purposes. For example, in some embodiments, the liquid in compartment 306 can dilute a sample. In other embodiments, the liquid in compartment 306 can adjust the pH of a sample. In yet other embodiments, the liquid in compartment 306 can contain sterilized broth that facilitates growth of microbes present in the sample. The volume capacity of compartment 306 can range from about 1 mL to about 24 mL, preferably from about 3 mL to about 5 mL, more preferably, about 4 mL.

In embodiments where pressure is applied to chamber 306, the liquid there is forced into sample holder 302 and forces the sample to discharge through 3044 and then through a one-way valve 314. The sample holder 302 discharges its content via tube 3042 into filtration unit 310. Filtration unit 310 comprises of several chambers separated by filters and configured with one-way valves 314 assuring no backflow of liquid after filtration. The content of sample holder 302 is discharged into receiving chamber 320. Adjacent to receiving chamber 320 is the microbe chamber 322. Chambers 320 and 322 are separated by a filter 324. Filter 324 has a filter size selected in such way that microbes can pass through the filter into chamber 322, while insoluble material, particles, human or animal cells, and biological matter larger than the filter size remain in receiving chamber 320. The filter material can be any suitable material. For example, the filter material can be cellulose, polymer, or glass fiber. For example, in embodiments, the filter material can be polyvinylidene fluoride (PVDF) membrane. The PVDF membrane can have a cellulose ester (RW06) prefilter layer. In embodiments, filter 324 can have a filter size of not greater than 0.45 microns, not greater than 0.5 microns, or not greater than 0.6 microns. In other embodiments, filter sizes for filter 324 that are not greater than 0.8 microns, or 1.0 microns, or even 2.0 microns are contemplated.

Adjacent to microbe chamber 322 is phage chamber 330, which is separated by filter 326. Contrary to filter 324, filter 326 has a filter size selected in such way that microbes do not pass through the filter into chamber 330, while material smaller than the filter size flow from chamber 322 into chamber 330. Such material includes wild-type phage present in the sample. The filter material of filter 326 can be any suitable material. For example, the filter material can be cellulose, polymer, or glass fiber. For example, in embodiments, the filter material can be polyvinylidene fluoride (PVDF) membrane. The PVDF membrane can have a cellulose ester (RW06) prefilter layer. In embodiments, filter 326 can have a filter size of not greater than 0.1 microns, not greater than 0.2 microns, or not greater than 0.45 microns. In other embodiments, filter sizes for filter 324 that are not greater than 0.5 microns, or 0.6 microns, or even 0.7 microns are contemplated Adjacent to phage chamber 330 is located waste chamber 332 separated by filter 328. Contrary to filters 324 and 328, filter 328 has a filter size selected in such way that wild-type phage do not pass through the filter into chamber 332, while material smaller than the filter size flow from chamber 330 into chamber 332. The filter material of filter 328 can be any suitable material. For example, the filter material can be cellulose, polymer, or glass fiber. For example, in embodiments, the filter material can be polyvinylidene fluoride (PVDF) membrane. The PVDF membrane can have a cellulose ester (RW06) prefilter layer. In embodiments, filter 328 can have a filter size of not greater than 0.05 microns, not greater than 0.1 microns, or not greater than 0.2 microns. In other embodiments, filter sizes for filter 328 are not greater than 0.3 microns, or 0.4 microns or even 0.45 microns are contemplated.

Although not depicted in FIG. 3, the flow of liquid from chamber 320 through filter 324 into chamber 322 or the flow of liquid from chamber 322 through filter 326 into chamber 330, as well as the flow of liquid from chamber 330 through filter 328 into chamber 332 can be regulated by one-way valves, to avoid backflow of liquids into the previous chamber.

Analyte chamber 308 contains an analyte solution and is in connection with microbe chamber 322. The analyte solution is the supportive of the microbes, once mixed it forms the microbe sample which will be analyzed for identity, count, or antimicrobial resistance. The analyte solution flows directed by one-way valve 314 then into chamber 322 and thereby immersing microbes present from the filtration of the donor sample. The analyte solution includes ingredients that support the viability of the microbes. For example, the analyte solution can contain a broth, a diluted broth, a buffer, or a buffer mixed with a broth. The same solution can also be contained in chamber 312.

Upon immersion of microbes in chamber 322 by the analyte solution to form the microbe sample, the microbe sample flows from chamber 322 into manifold 316, which distributes the sample evenly over a number of wells 318. The number of wells 318 can be between 2 to 24, preferably, 8 to 20, preferably about 18. Regardless of the total number of wells, at least one well does not receive the microbe sample but receives analyte solution from chamber 312. This well is designated the control well. Each well 318 is equipped with at least two electrodes, the electrodes are connected to a stackable interface 320, which connects with reader unit 204.

The electrodes in the wells can be made of any known electrode material. In embodiments, the electrode material can be coated with a material that increases the sensitivity of the electrode. In embodiments, the electrode material can be coated with noble metals such as gold, platinum, or palladium. The electrodes should be made from non-oxidizing material and may consist of several metal and non-metal materials. In other embodiments, the electrode material is copper coated with a special formulation of graphene. The copper coating and graphene creates a non-oxidizing, highly conductive electrode.

In one embodiment, an aqueous dispersion of graphene can be prepared by catalytic hydrogenation of humic acid. Humic acid can be extracted from leonardite (Agro-Lig) and then catalytically hydrogenated. Catalytic hydrogenation can be done using various catalysts in a Parr reactor at 150° C. The catalysts can be palladium or platinum metal or palladium on charcoal or platinum on charcoal. The dispersion can be passed through a strong acid ion exchange column to remove excess cations. The aqueous dispersion of graphene can be applied to electrodes, such as copper electrodes, gold electrodes, or silver electrodes. In embodiments, the graphene content of the aqueous dispersion can be 0.5% by weight. In another embodiment, the graphene content might be 1% by weight. And yet another embodiment the graphene content might be 2% by weight. In yet other embodiments, the graphene content can be about 0.1% by weight, about 0.2% by weight, about 0.5% by weight, about 0.8% by weight, about 0.9% by weight, about 1.0% by weight, about 1.5% by weight, about 1.8% by weight, about 2.0% by weight, or about 2.5% by weight.

Graphene prepared by this method has functional groups, such as hydroxyl groups bonded to the graphene. These functional groups have an affinity to bind the graphene to a metal and thus, improve the coating of the electrode with graphene. A graphene coated electrode improves resistance of the electrode to oxidation and also improves the conductivity property of the electrodes.

In some embodiments, the diagnostic device further includes a heating component, for heating the unit or compartments thereof. For example, a heating component, such as a heating coil, can be placed around microbe chamber 322, to control the temperature of the microbes sample.

In embodiments, the diagnostic unit, including a sample holder and a filtration unit can be used in combination with any analytical reader unit. For example, the diagnostic unit can be adjusted as sample preparation device for antimicrobial analysis, where the analysis is conducted by conventional methods, such as enzyme assays or fluorescent assay.

Figure 4:
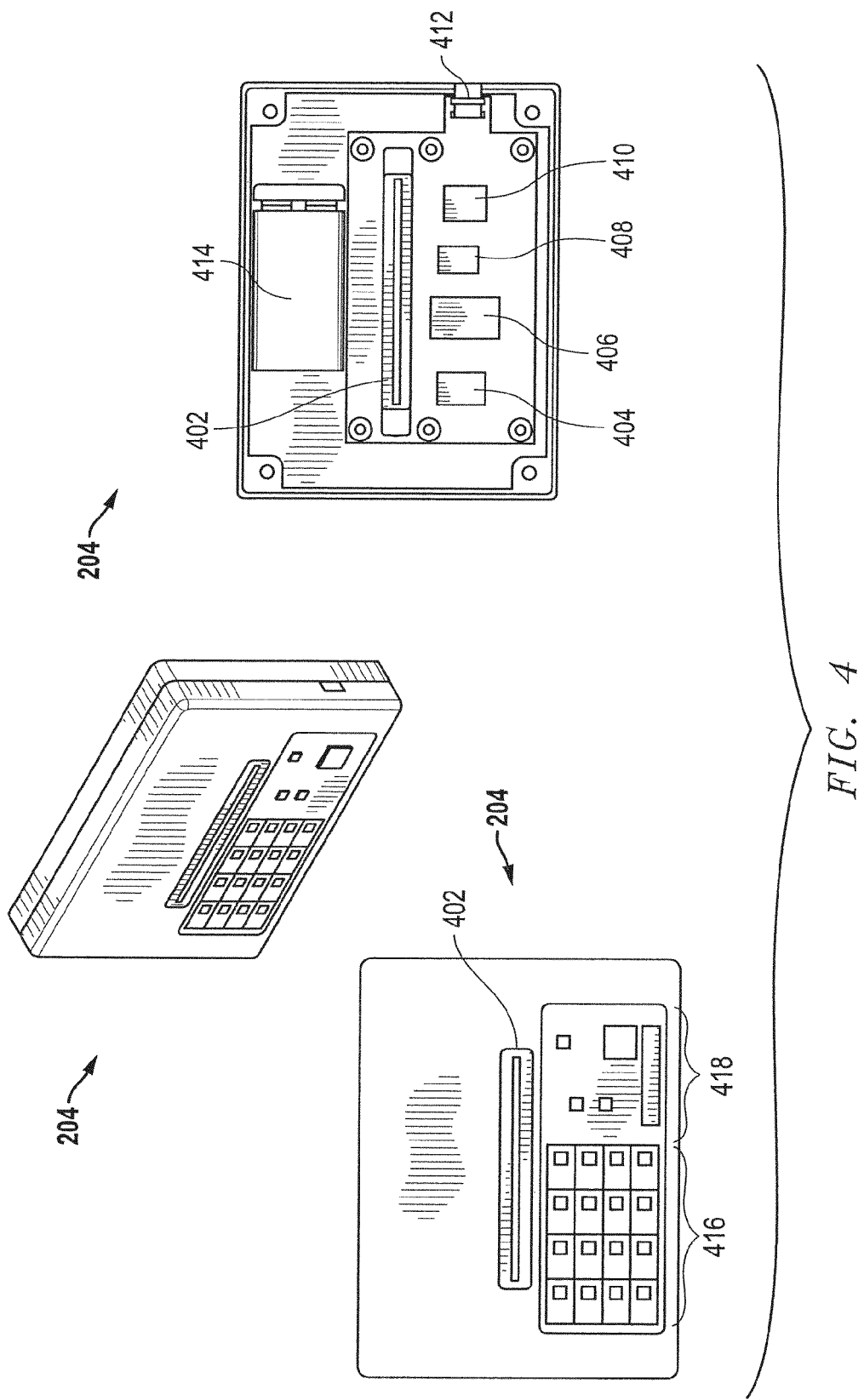
FIG. 4 includes an illustration of an embodiment of the reader unit of the diagnostic device.

FIG. 4 displays the reader unit 204. The reader unit has a card connector slot 402 to receive the stackable interface 320. The interior includes various electronic components. The interior includes an analog to digital (A/D) converter 404, a digital signal processor 406, a display processor 408, and a memory component 410. The reader has a clock unit which is not shown in diagram for controlling the sample-period and sample-duration. The reader can receive an input using communication port represented by 412 so the data being collected into memory component 410 can be associated with the patient. In some embodiments, the input mechanism can be integrated to the reader device. Some or all of these electronic components 404 through 410 can be consolidated into one component. The reader unit further includes a power source 414, such as a battery and a port 412 for transmitting data to another computing device where it can be stored as a database or further processed. The transmission through port 412 can occur directly through a wire into a computing device where it can be stored in a database or further processed. Alternatively, the transmission through port 412 can occur wirelessly through a wireless network, cellular network or the World Wide Web to reach an application for further processing, storing in a database or presented to a user. In embodiments, data obtained by the diagnostic device can be transmitted as a secured email or SMS to at least one user, such as a doctor or nurse. In other embodiments, data obtained from the diagnostic unit can be transmitted to other users or databases such as health care facilities, centers for disease control, or insurance companies. In other embodiments, port 412 may receive input directly associated with the patient to be stored in memory component 410 where it is used to associate the data to the patient.

The reader unit further includes a display, the display can be a well indicator field 416 which display, which well has signature associated with an attack or inhibition by an antimicrobial. Further the display can be associated with positive or negative bacteria identification. The well indicator field can be correlated with a template envisioned to be applied as a label to the first stackable unit. The indicator field might be lights but other embodiments are being contemplated.

The reader unit further can include a count output 418 that displays the measured count. The count can be displayed as a figure or as a meter light, which, for examples, shows more, bars the higher the count is. Further, there are displays to indicate that self-test diagnostics functioned properly and further that the battery is active. There is also an on/off button contained in area 418.

Upon inserting a biological sample into sample holder 302 of the diagnostic unit 202, the unit is inserted into card reader slot 402. In embodiments, the reader unit can additionally be equipped with a micro pump system that controls the flow of liquids through the diagnostic unit 202. In other embodiments, the reader unit controls one-way valves 314 to direct the flow of liquids through the diagnostic unit 202. In yet other embodiments, the reader unit controls the flow of liquids through the diagnostic with the help of a micro pump and individual control over one-way valves 314. In some embodiments, the card slot 402 can be located to facilitate side by side arrangement of 204 and 202. In some embodiments, 202 and 204 can be integrated into one unit and miniaturized according to the sample type.

Upon pretreatment of the biological sample to obtain a microbes sample in chamber 322, the microbes sample is distributed into a number of wells 318, while at least one well serves as a control and contains only analyte solution form compartment 312. At this point, the diagnostic device can sample data in accordance with the sampling method described herein.

In embodiments, where a count is determined, the reader unit samples an electrical property such as conductance, resistance, voltage, amperage, capacitance, impedance, inductance, or any combinations thereof to create a digital signature.

In embodiments where identity of a microbe in a microbial sample is determined, the wells 318 of the diagnostic unit contain bacteriophages, mycoviruses, virophages, or nematophages. These phages are specifying in attacking bacteria, fungi, viruses, or nematodes, respectively. The phages are present in the wells before a biological sample is applied to the diagnostic unit.

In embodiments, each well that receives bacteria sample contains a different bacteriophage. Bacteriophages only attack bacteria having the appropriate binding sites. Accordingly, bacteriophages can be chosen for specific bacterium so that it will only attack that bacterium. Once a bacteriophage attacks bacteria, a signal in the sampling can be observed. Therefore, by measuring bacteriophage attacks of one or more bacteriophages onto the bacteria sample, one can obtain conclusive data as to the percentage of bacteria species present in the sample and the identity of such bacteria.

Some embodiments might use other types of phages to identify other types of microbes. For example, if the microbe is a fungus, a mycovirus can be used to identify the microbe. In other embodiments, virophages or nematophages can be used to identify viruses or nematodes.

In embodiments, the bacterial identification feature can be implemented with only one well, but may consist of more wells for increased accuracy. At least one well contains the sample with bacteriophage specific to the bacterium being identified. Bacteriophage can be selected to attack one-and-only-one bacterium. In yet other embodiments, bacteriophages may be combined to create a phage-cocktail which can be used to identify a group of bacteria.

In embodiments, where antibiotic resistance or antimicrobial resistance of a microbes sample is determined, the wells 318 of the diagnostic unit contain antibiotics or antimicrobials and at least one well contains the microbial sample as a control well. These antibiotics or antimicrobials are present in the wells before a biological sample is applied to the diagnostic unit. In embodiments, each well that receives microbes sample contains a different antibiotic or antimicrobial. Antibiotics or antimicrobials work differently for different strains or species of microbes. Once a microbe colony stagnates or dies from an antibiotic or antimicrobial present in the well, a signal of this particular well in the sampling can be observed. Therefore, by measuring antibiotic or antimicrobial activity of one or more antibiotics or antimicrobial onto the microbial sample, one obtains conclusive data as to the antibiotic or antimicrobial susceptibility of the microbial species present in the sample. On the other hand, for wells where there is no antibiotic or antimicrobial activity, and the control well shows microbial viability, then one observes antibiotic resistance or antimicrobial resistance of the microbe sample.

In embodiments, the antimicrobial sensitivity test requires at least two sensor-wells. At least one sensor-well contains a control sample consisting of the microbial sample, i.e. microbes immersed in analyte solution. The other sensor contains the sample with the antibiotic or antimicrobial being tested for effectiveness. At the end of the sample-duration, the colony count of the control sample will be compared against the beginning colony count and if there were microbes the count will have increased by the end of the sample-duration. When there is no growth of microbes in the control sample, then the results from the sample with the antibiotic or antimicrobial will be suppressed to support the observation that the microbes was not active and therefore not in need of antibiotic or antimicrobial treatment. Otherwise, the results from comparing the antimicrobial sample's digital signature created during the sample-duration will be analyzed and reported. Digital signature is further described herein.

In embodiments, two cells both containing samples from the same source can be compared to quantify the effectiveness of an antimicrobial by placing antimicrobial in one cell along with the sample and after a time period releasing bacteriophage also into that cell (Cell AP) and measuring the signal in the sampling and comparing it against the sampling signal in another cell with only bacteriophage released. (Cell P). The difference in the signals of the cells divided by the signal of the sample signal of the second cell will indicated the percentage of bacteria killed by the antimicrobial. (Cell P−Cell AP)/Cell P; where Cell P is the signal strength of the cell after adding bacteriophage to the sample; Cell AP is the signal strength determined when the bacteriophage are added after waiting a time period after the antibiotic have been added.

In yet other embodiments, the diagnostic system may consist of one or any combination of the features: bacterial identification, microbial colony counter, or antimicrobial sensitivity test. For example, some wells may contain no additives, such as phage or antimicrobials, some wells may contain phages, and some wells may contain antimicrobials or antibiotics. Such assembly facilitates the analysis for count, identity, and treatment with an antibiotic or antimicrobial of a microbial sample.

3. Digital Signature

A digital signature consists of data captured during the sample-duration and is a distinctive curve. Digital signal processing pattern matches across the distinctive digital signature to arrive at a pattern match. The distinctive digital signatures are recorded in a database based on earlier characterization. In embodiments, digital signatures are based on capturing changes in electrical properties such as the average resistance of the test sample as a function of time. In some embodiments the digital signature can be determined without pattern matching, but using other functional analysis.

In general, the reader unit is able to detect the change in concentration of live microbes based on changes in the resistance of the microbial sample, i.e. microbes immersed in the analyte solution. In embodiments, there are other distinctive digital signatures. For example when a bacteriophage attacks a bacterium, up to $10^8$ potassium ions can be released from the bacteria followed by reabsorption of the ions by the bacteria, which creates a distinctive change in measured resistance with time.

Each life event of the microbes has a distinctive pattern. For example, growing microbes multiply and create less resistance because they emit protons and ions of potassium, calcium and sodium as part of their natural respiration and metabolic process. For example, bacteria multiply every twenty minutes and this life event can be detected by constantly decreasing resistance measurements.

4. Microbial Count

Figure 5A:
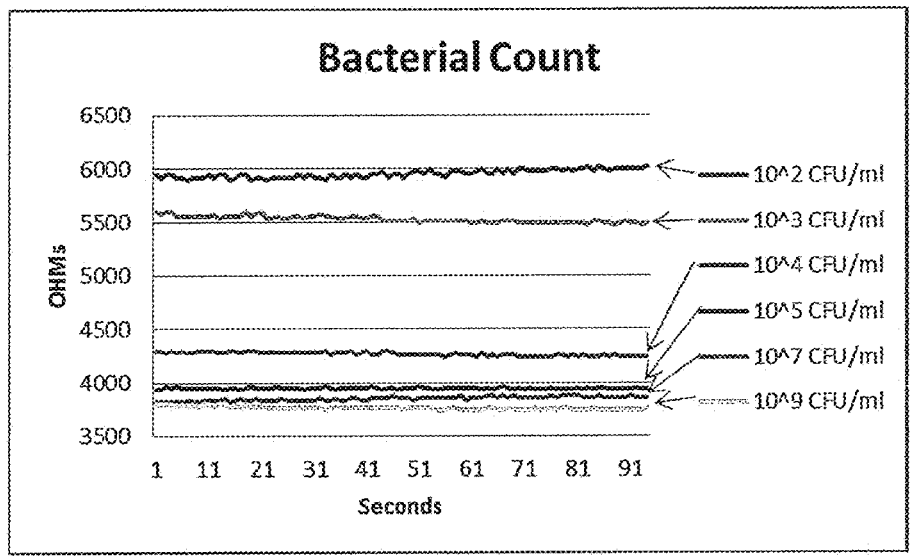
FIG. 5. include a plot of signatures at various microbial counts of colony forming units per mL.
Figure 5B:
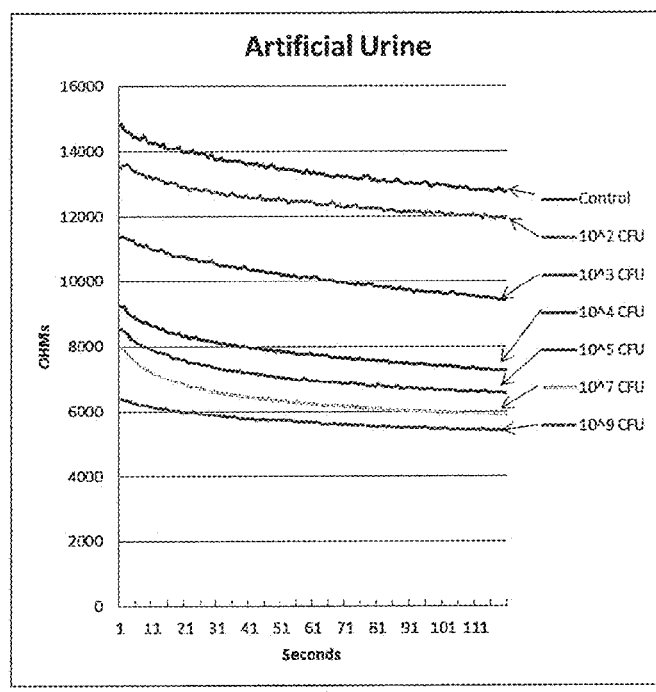

FIG. 5a depicts resistance measured of samples containing various concentrations of colony forming units (CFU) of *E. Coli* B suspended in LB Broth. FIG. 5b depicts resistance measured of samples containing various concentrations of colony forming units (CFU) of *E. Coli* B suspended in artificial urine. Samples have the following concentration: $10^2$ CFU/mL, $10^4$ CFU/mL, $10^5$ CFU/mL, $10^6$ CFU/mL, $10^7$ CFU/mL and $10^9$ CFU/mL. FIG. 5 clearly show that samples have distinctive resistance component of total impedance over time. Samples can be distinguished by their average resistance value. In embodiments, this feature is employed to determine the concentration of a microbial sample and correlate such concentration under consideration of the volume of the biological sample placed in the sample holder to a count or concentration present in the biological sample. This feature is also employed to determine microbial viability.

5. Bacterial Identity

Figure 6:
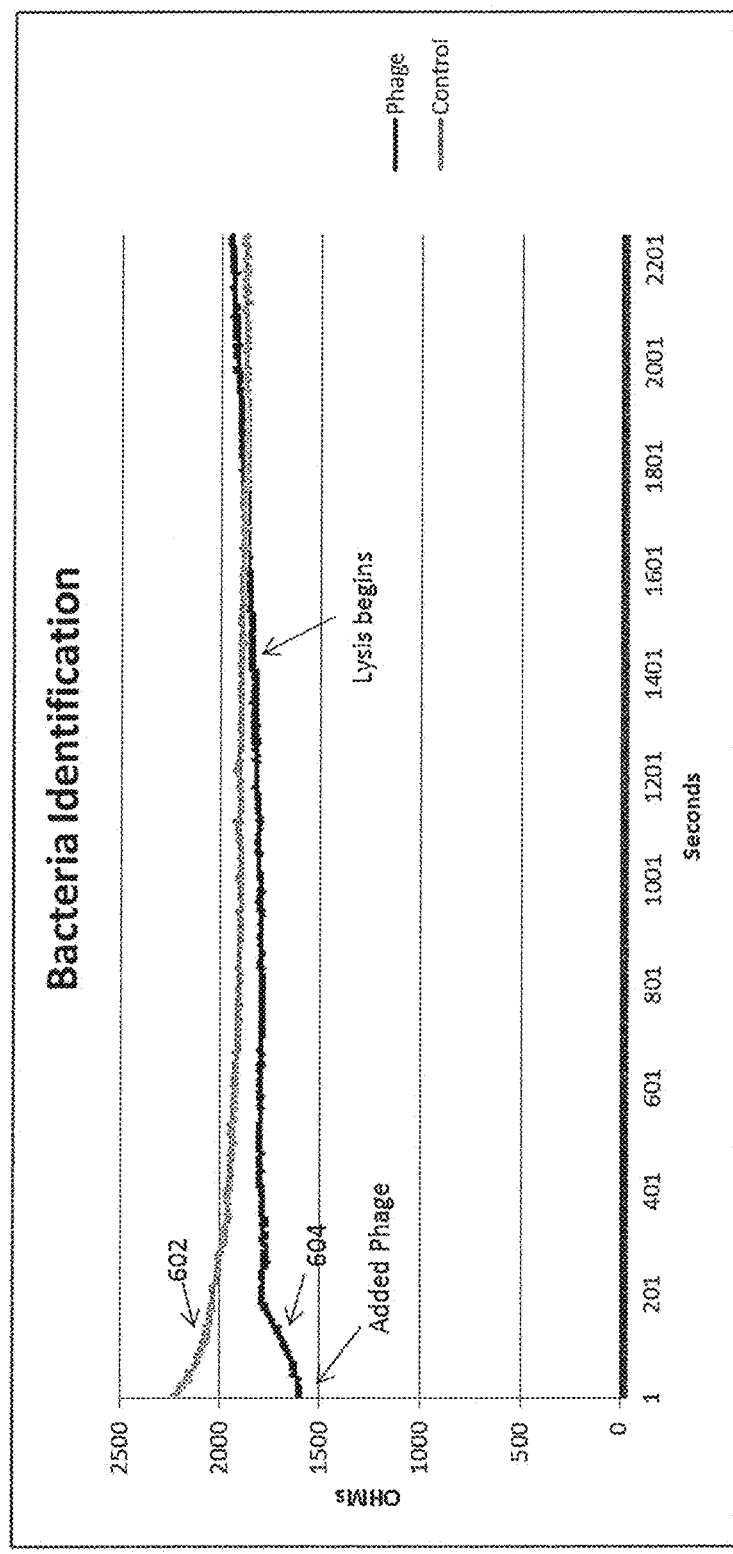
FIG. 6 includes plots of signatures showing a phage attack on bacteria, the second signature showing the control, bacteria in the absence of a phage.
Figure 7A:
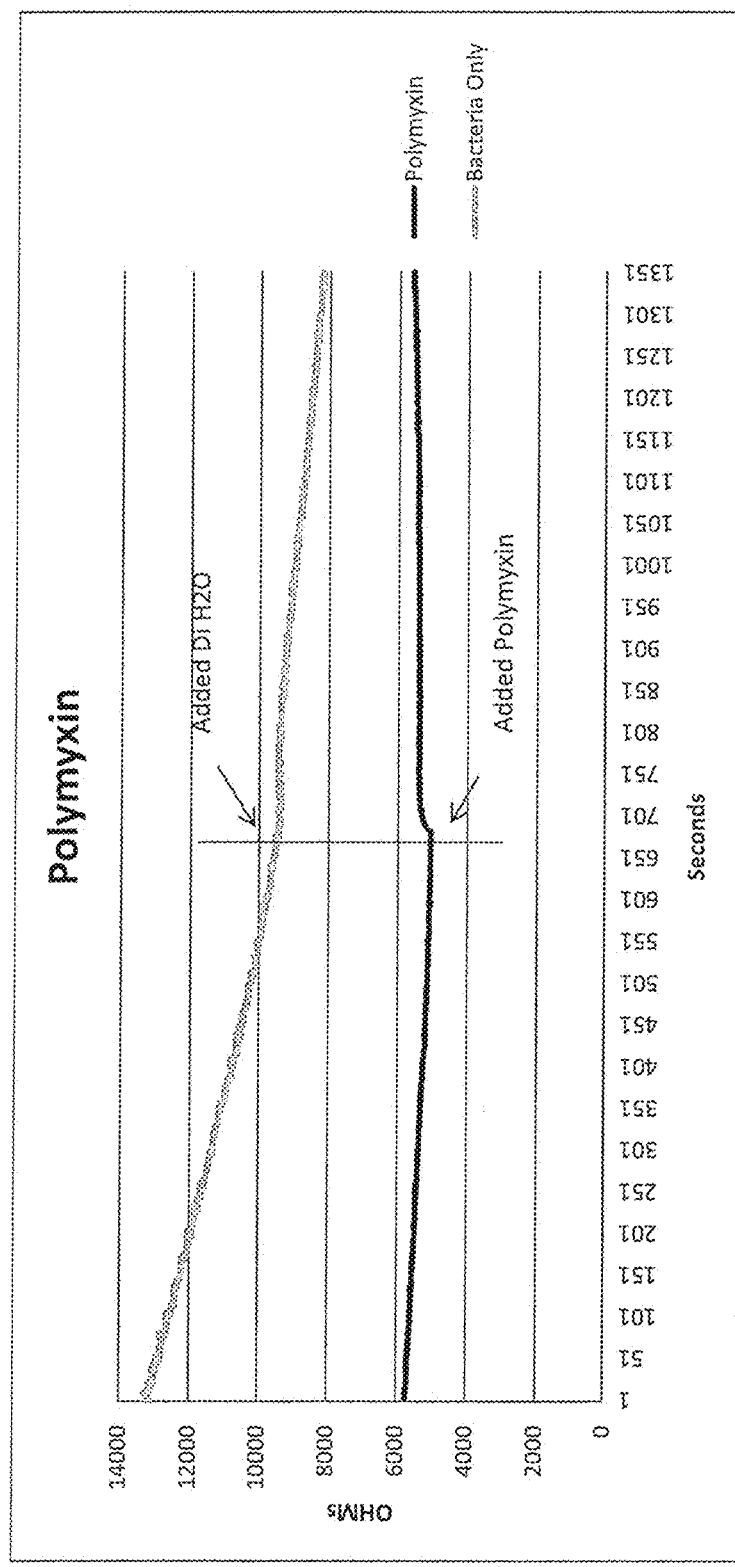
FIG. 7 include plots of signatures for microbes being treated with different antimicrobial agents.
Figure 7B:
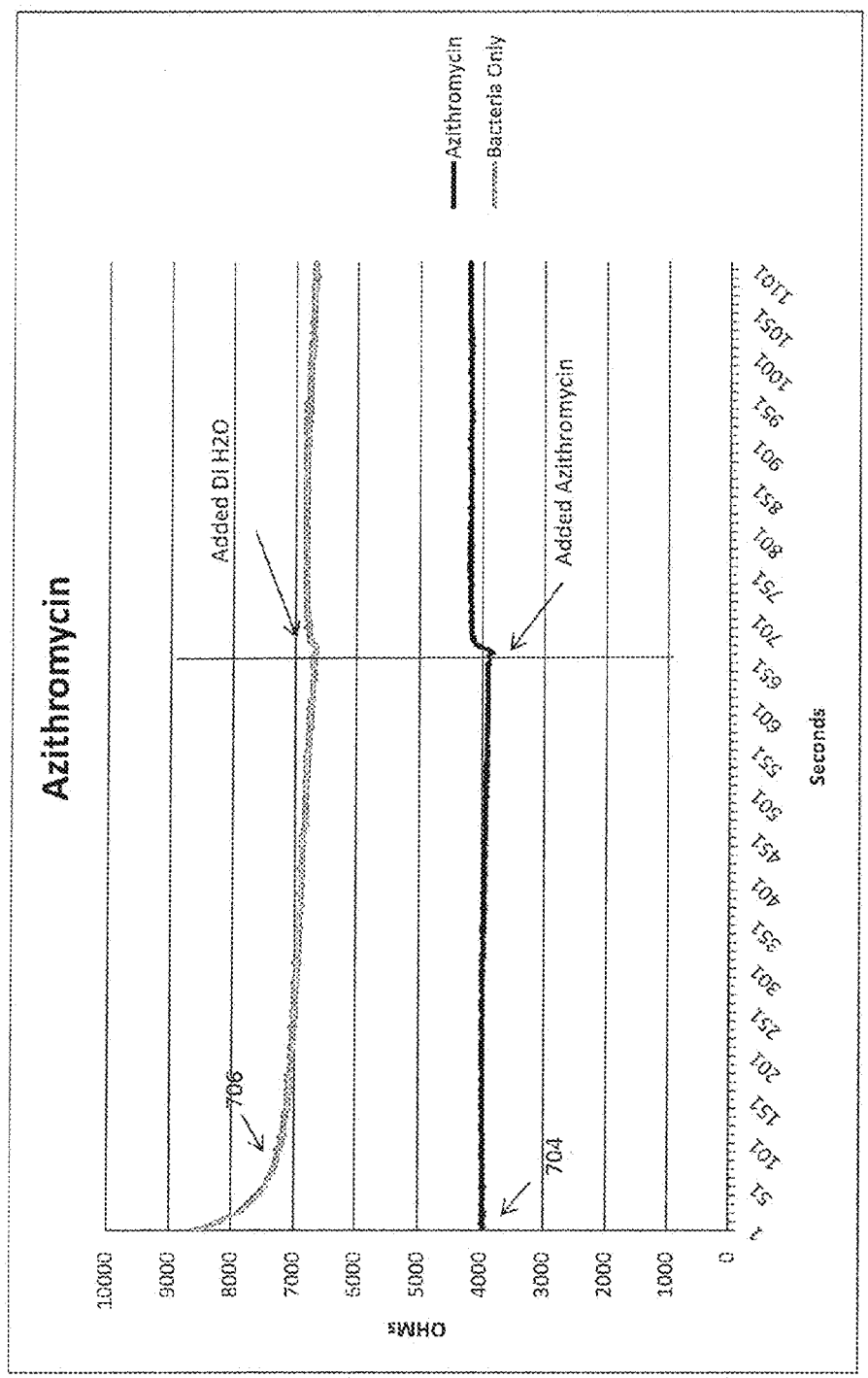
Figure 7C:
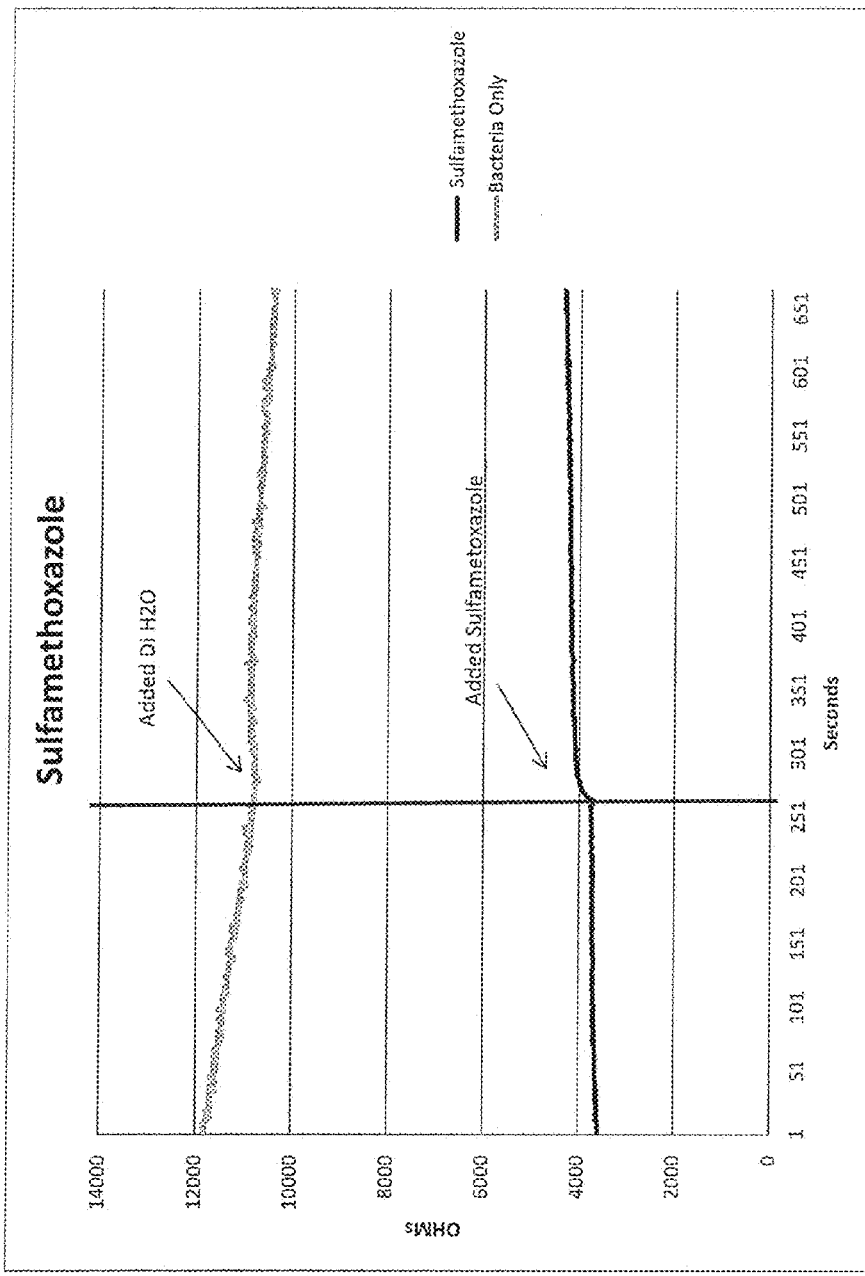
Figure 7D:
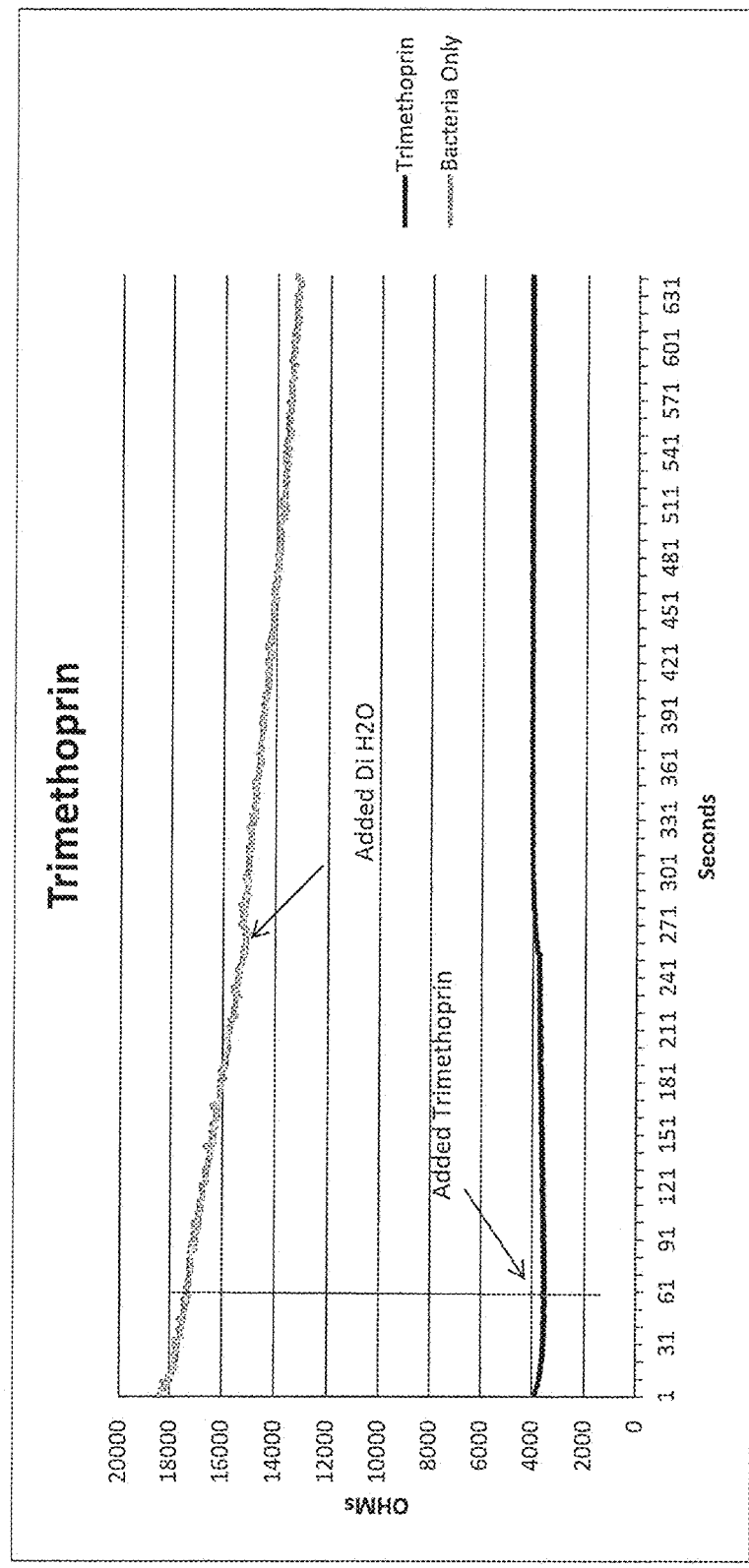

FIG. 6 depicts the signature of a sample of $10^8$ CFU/ml *E. Coli* B in an analyte of LB Broth for a final volume of 0.9 mL being attacked by 0.1 mL concentration of $1.62 \times 10^{11}$ T4 phage and a control sample in the absence of a phage. Signature 602 displays the course of a control sample not containing a phage. Initially, the sample rapidly reduces in resistance due to a fast growth of colonies in the sample, which contains some broth. The signal was captured just as the bacteria slow their growth. The resistance component of total impedance value levels off into a linear course as the bacteria growth begins to slow down due to the limited resources of nutrients in the sample. The control sample maintains the linear slope for at least more than 20 minutes (or 1200 seconds). The last section of signature, starting at about 1401 seconds shows a slight increase in resistance, indicating that the bacteria population reduces in numbers.

On the other hand, signature 604 of FIG. 6 shows the signature of a microbial colony of *E. Coli* B under phage attack. Phage attack is initiated by adding phage before the data are being collected and at the point indicated on the graph. The phage attack is instantaneous and is already in progress before the sample duration was initiated and the bacteria have each released up to $10^8$ potassium ions causing a rapid drop in resistance of the analyte. Within the next 200 seconds following the phage attack, there is a rise in resistance component of total impedance, indicating that the colony is attempting to recover from the attack by reabsorbing the potassium ions that the phage attack caused the bacteria to release. After about 200 seconds, the phage attack is over and the signature levels off. During the course of the next 20 to 25 minutes, a positive slope of the signature can be observed, indicating that the bacteria colony is inhibited in its growth. Furthermore, an increase in the slope of the signature can be observed at about 1400 seconds. This is approximately the time at which phages have replicated and begin to lyse the bacteria colony.

Comparing signatures 602 and 604 in FIG. 6, a sample containing a known phage specific to a certain strain or species of bacteria can be used to identify whether the sample contains this specific bacteria colony. Likewise, if a sample contains two types of bacteria distinct in strain or species, an assay of sampling these bacteria against different phages can identify the presence of each strain or species, independently.

6. Antimicrobial Resistance

FIGS. 7a-7d depict signatures of microbial sample of 0.9 mL of a concentration of $10^3$ CFU/mL of two-hour *E. Coli* B treated with 0.1 mL of antibiotics or antimicrobials and control samples in the absence thereof. What is common to all FIG. 7 is the slope for signatures with antibiotics or antimicrobials become positive, i.e., the resistance component of total impedance of the microbial sample increases, upon addition of the antibiotic or antimicrobial. The slope of the control samples remains negative.

In further detail, a difference in the degree of the slope change for the signature can be observed. Such differences are due to the type of antibiotic or antimicrobial, and its mechanism of action. For example, sulfamethoxazole, FIG. 7c, causes inhibition of DNA synthesis in the cell, thereby aiming essential cell functions. In contrast, azithromycin, FIG. 7b, inhibits protein inhibition in a bacterium, thereby acting on latent cell functions. As a result, the slope of the signature for sulfamethoxazole is steeper than for azithromycin, because the microbial colony treated with the former is expected to die faster.

7. Technical Preparation of a Reader Unit

Figure 8A:
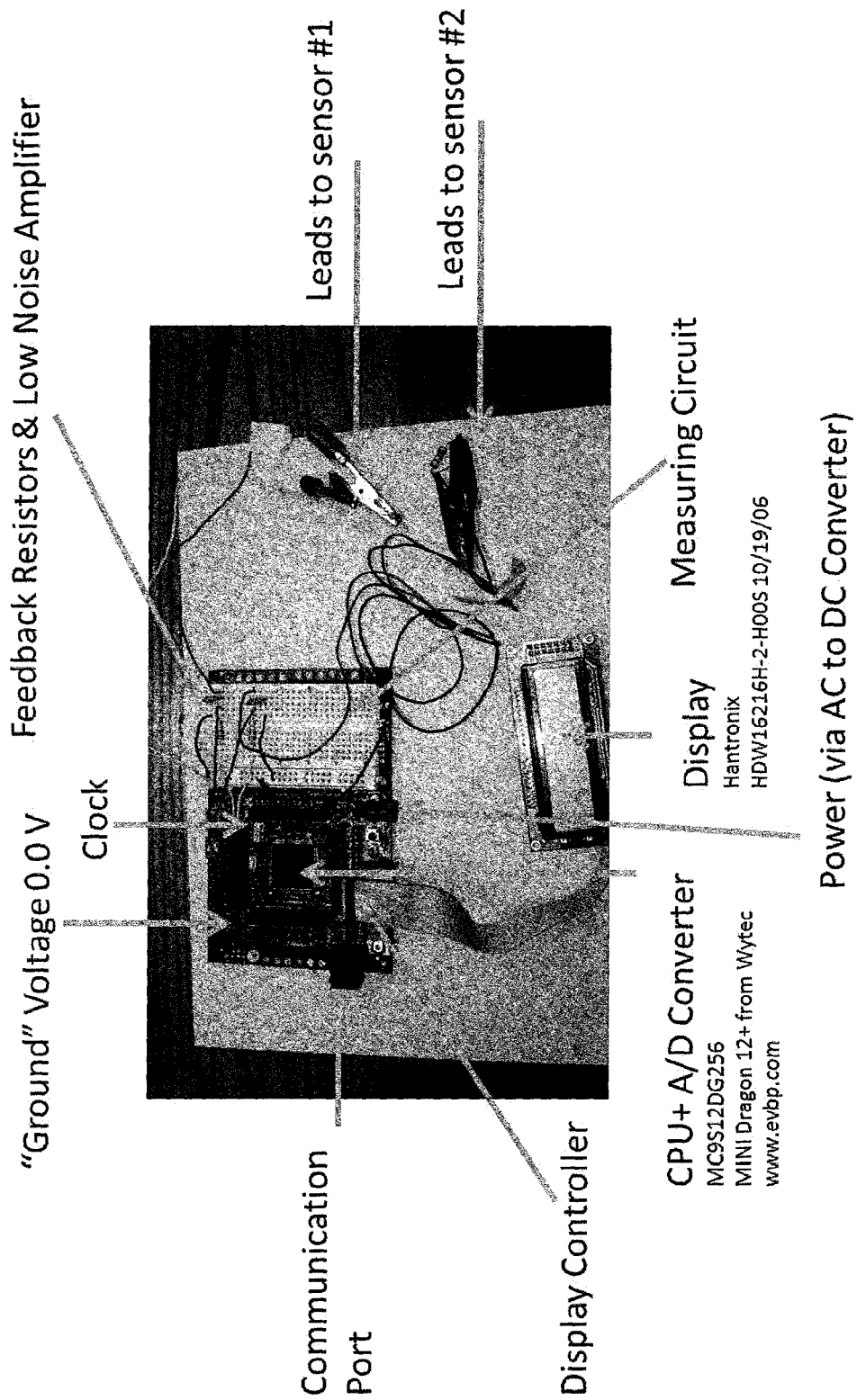
FIG. 8 include an illustration of a technical set-up of a reader unit.
Figure 8B:
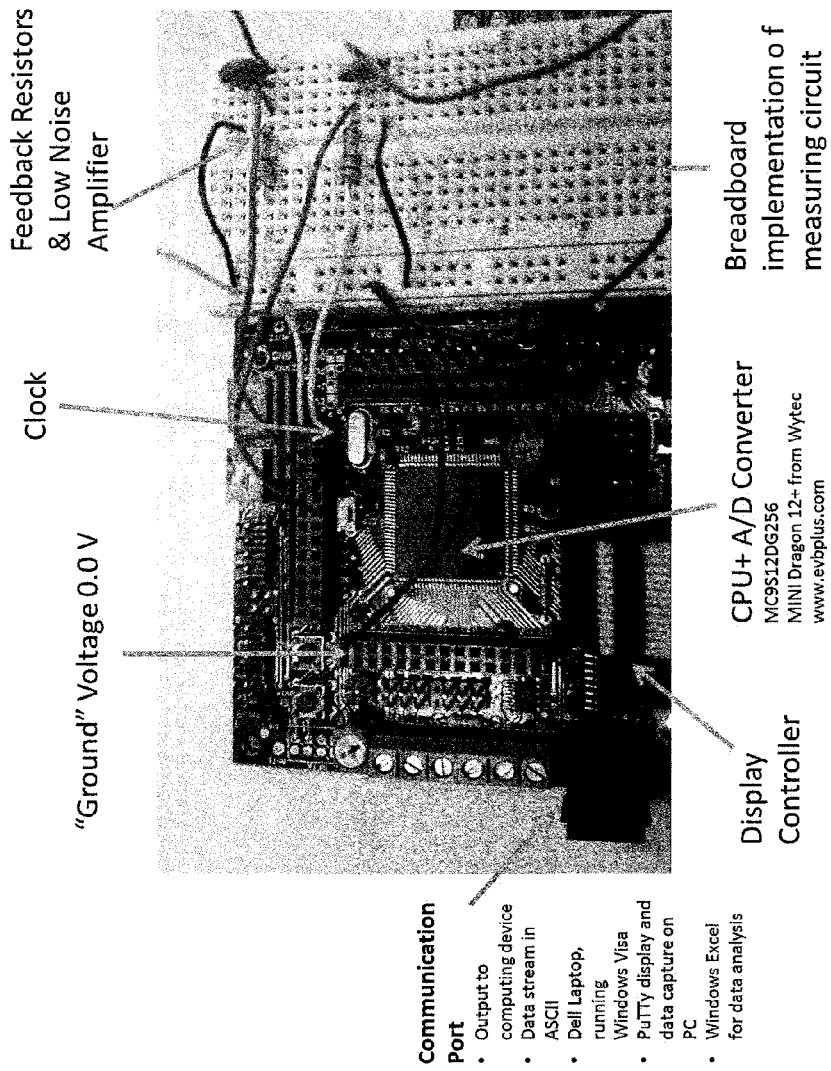
Figure 8C:

FIG. 8 displays an implementation of a reader unit having two leads. The leads are connected to the electrodes of the sample well. The reader unit as shown in FIGS. 8a and 8b controls the sampling and recording of data. In embodiments, a sample well or sample tube as for example depicted in FIG. 8c, includes a container equipped with electrodes (not visible in FIG. 8c) and contacts on the outside of the tube to which the reader unit can be connected. In one embodiment, the electrodes can be copper wires coated with graphene from a 2 wt % graphene solution to form a non-corrosive yet conducting surface on the copper wire. A control well contains the same ingredients as the sample well with the exception of the microbe and both wells are connected to the leads depicted in FIG. 8a as sensors #1 and #2, respectively. Data is collected by way of the sampling method described herein. The reader unit includes a feedback resistor and low noise amplifier, a display with a display controller and a central processing unit (CPU) which also may house an analog to digital (A/D) converter. The communication port can transmit data to another computer for analysis.

In embodiments, the communication port is a POTS phone connection. Another embodiment implemented was a USB connection. Another embodiment is envisioned as a connection to other direct wired ports used by other computing devices which may be laptops, desktops, notebooks, tablets, mini-PC, mini-tablets, and cell phones or other such devices.

Another embodiment is contemplated to be a wireless connection. Yet another embodiment is envisioned to be a cellular connection. Both embodiments are envisioned as a connection to other wireless ports used by other computing devices which may be laptops, desktops, notebooks, tablets, mini-PC, mini-tablets, and cell phones or other such devices.

Other embodiments may communicate with a Smartphone providing final results. Yet other embodiments might stream data to a Smartphone so the Smartphone might analyze the data and send resulting data to user via secured email or SMS messages.

Other embodiments may communicate with a Smartphone providing parameter inputs to the diagnostic device. Additionally other embodiment might download patient information to be stored with results for later transmission by diagnostic device along with the data or results from the diagnostic reader unit.

Another embodiment is envisioned to connect to the World Wide Web with an application on a server to analyze the data and store it in a database. It is envisioned that the application can further interface to other applications as a software-as-a-service application. In this embodiment a fee-for-service can provide healthcare workers and antibiotic manufacturers with regional demographics of antibiotic resistant microbes and antibiotic use collected from statistics using depersonalized results of accumulated diagnostic results. Another embodiment will place antibiotic advertising on the labeling of the diagnostic kit.

Another embodiment might receive input commands from a computing device via the communication port. Additionally other embodiment might download patient information to be stored with results for later transmission by diagnostic device along with the data or results from the diagnostic reader unit.

Many different aspects and embodiments are possible. Some aspects and embodiments are described below. After reading this specification, skilled artisans will appreciate that those aspects and embodiments are only illustrative and do not limit the scope of the present invention.

In one aspect, a method for determining antimicrobial activity of an agent includes providing a well, wherein the well contains one or more antimicrobial agents. The well further includes at least two electrodes. The method further includes adding a sample of at least one microbe into the well, pulsing voltage between the electrodes, sampling an electrical property during the pulsing, and recording the electrical property.

In embodiments, the method further includes repeating the pulsing, the sampling and the recording, and plotting the recordings versus time to form a signature. In other embodiments, the method further includes that the microbes are selected from bacteria, fungi, viruses, or nematodes. In other embodiments, the method may include one or more antimicrobial agents selected from bacteriophages, mycoviruses, virophages, nematophages, antibiotics, antimicrobials, antivirals, antifungals, or parasiticides. Bacteriophages, mycoviruses, virophages, nematophages are viruses that attack bacteria, fungi, viruses, and nematodes, respectively. In yet other embodiments, the method further comprises measuring a temperature inside the well. The temperature can be measured with a thermistor.

The pulsing of the method includes an on-period and an off-period, the sum of the on-period and the off-period comprises a sample-period. In embodiments, the on-period is at least about 1 millisecond, at least about 2 milliseconds, at least about 3 milliseconds, at least about 5 milliseconds, at least about 10 milliseconds, at least about 15 milliseconds, at least about 20 milliseconds, at least about 50 milliseconds, at least about 100 milliseconds, at least about 200 milliseconds, or at least about 500 milliseconds. In other embodiments, the off-period is at least about 100 milliseconds, at least about 200 milliseconds, at least about 500 milliseconds, at least about 1 second, at least about 2 seconds, at least about 3 seconds, at least about 5 seconds, at least about 10 seconds, at least about 20 seconds, at least about 40 seconds, at least about 50 seconds, or at least about 60 seconds. In other embodiments, the on-period is not greater than about 500 milliseconds, not greater than about 200 milliseconds, not greater than about 100 milliseconds, not greater than about 50 milliseconds, not greater than about 20 milliseconds, not greater than about 10 milliseconds, not greater than about 5 milliseconds. In yet other embodiments. the off-period is not greater than about 60 seconds, not greater than about 30 seconds, not greater than about 10 seconds, not greater than about 5 seconds, not greater than about 2 seconds, not greater than about 1 second, not greater than about 500 milliseconds, not greater than about 200 milliseconds, not greater than about 100 milliseconds, not greater than about 50 milliseconds. In yet other embodiments, the sample-period is about 1 second, about 5 seconds, about 10 seconds, about 20 seconds, about 30 seconds, about 40 seconds, about 50 seconds, about 60 seconds.

In embodiments, the voltage is at least about 0.0005 V, at least about 0.001 V, at least about 0.002 V, at least about 0.005 V, at least about 0.01 V, at least about 0.02 V, at least about 0.05 V, at least about 0.1 V, at least about 0.2 V, at least about 0.5 V, at least about 1.0 V, at least about 2.00 V, at least about 5.0 V, or at least about 10.0 V. In other embodiments, the voltage is not greater than about 2.0 V, not greater than about 1.0 V, not greater than about 0.5 V, not greater than about 0.2 V, or not greater than about 0.1 V. In further embodiments, the voltage is ranging from about 0.0005 V to about 2.0 V, from about 0.0005 V to about 1.0 V, from about 0.001 V to about 1.0 V, from about 0.05 V to about 1.0 V, from about 0.05 V to about 0.5 V, or from about 0.05 V to about 0.1 V.

In embodiments, the sampling of the electrical property occurs during the sample-period. Yet, in other embodiments, the sampling of the electrical property is at least about 0.5 milliseconds, at least about 1 millisecond, at least about 2 milliseconds, at least about 3 milliseconds, at least about 5 milliseconds, at least about 10 milliseconds, at least about 15 milliseconds, at least about 20 milliseconds, at least about 50 milliseconds, at least about 100 milliseconds, at least about 200 milliseconds, or at least about 500 milliseconds. In further embodiments, the sampling is not longer than about 360 minutes, not longer than about 180 minutes, not longer than about 120 minutes, not longer than about 90 minutes, not longer than about 60 minutes, not longer than about 45 minutes, not longer than about 30 minutes, not longer than about 20 minutes, not longer than about 10 minutes, not longer than about 5 minutes, or not longer than about 2 minutes. In yet other embodiments, the sampling is between about 15 seconds and about 60 minutes, between about 15 seconds and about 45 minutes, between about 15 seconds and about 20 minutes, between about 15 seconds and about 10 minutes, between about 1 minute and about 20 minutes, between about 2 minutes and about 20 minutes, between about 5 minutes and about 20 minutes, between about 5 minutes and about 10 minutes, or between about 10 minutes and about 20 minutes.

In another aspect, a method for identifying at least one microbe includes taking a sample containing the at least one microbe, isolating the at least one microbe from the sample, dividing the at least one microbe into a number of wells, wherein each well contains at least one antimicrobial agent and at least two electrodes. The method further includes pulsing a voltage between the at least two electrodes, sampling an electrical property during the pulsing; and recording the electrical property for a sample-duration.

In embodiments, the isolating of the method further includes filtering the sample to separate the at least one microbe from the sample, and immersing the at least one microbe in an analyte. The analyte is selected from water, buffer, saline, broth, or any combination thereof. The microbes are selected from bacteria, fungi, viruses, or nematodes. The antimicrobial agents are selected from bacteriophages, mycoviruses, virophages, nematophages, antibiotics, antimicrobials, antivirals, antifungals, or parasiticides.

In another aspect, a method for determining a count of microbes in a sample includes filtering the sample to separate the at least one microbe from the sample, immersing the at least one microbe in an analyte to form an immersion, incubating the immersion for a specific time, dividing the immersion into a number of wells, measuring an electrical property in the wells for a sample-duration, and correlating the electrical property to a count. In embodiments, the method further comprises adding at least one bacteriophage to at least one of the wells before measuring the electrical property.

In embodiments, the sample-duration is at is about 1 second, about 5 seconds, about 10 seconds, about 20 seconds, about 30 seconds, about 40 seconds, about 50 seconds, about 60 seconds. In other embodiments, the specific time for the incubating is at least about 0.5 seconds, at least about 1 second, at least about 30 seconds, at least about 1 minute, or at least about 2 minutes. In other embodiments, the specific time for the incubating is not longer than about 1 millisecond, not longer than about 1 minute, not longer than about 2 minutes, not longer than about 5 minutes. In yet other embodiments, the specific time for the incubating is between 1 millisecond and 5 minutes, between 0.5 second and 2 minutes, between 1 second and 1 minute.

In another embodiment, the method determines a first count for a first microbe and a second count for a second microbe.

In one further aspect, a method for determining antimicrobial resistance of a microbe includes adding a sample of at least one microbe into a well containing at least one antimicrobial, and measuring an electrical property in the well for a sample-duration. The sample-duration is at least one hour and not more than six hours.

In embodiments, the microbes are selected from *Aerobacter, Bacillus, Bordetella, Brucella, Campylobacter, Chlamydia, Chromobacterium, Clostridium, Corynebacterium, Enterobacter, Escherichia, Haemophilus, Klebsiella, Listeria, Mycobacterium, Mycoplasma, Neisseria, Pneumococcus, Proteus, Pseudomonas, Providencia, Salmonella, Serratia, Shigella, Staphylococcus, Streptococcus, Vibrio, Yersinia, Acinetobacter, Bacteroides, Bifidubacterium, E. kenella corrodens, Gardnerella vaginalis, Mobiluncus, Proteobacteria, Desulfobacterales, Desulfovibrionales, Syntrophobacterales, Thermodesulfobacteria, Nitrospirae*, gram positive *Peptococcaceae, Archaea, Archaeoglobus*, or any combinations thereof.

In other embodiments, the antimicrobial agents are selected from *Actinomyces* phages, *Bacillus* phage Φ29, bacteriophage M102, bacteriophage e10, bacteriophage f1, bacteriophage λ, bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, ssRNA bacteriophages Q beta, *S. mutans* phages, and any combinations thereof.

In other embodiments the phage is cultivated and isolated so that it attacks only the microbe to be identified using methods well known to those in the field of microbiology. Such phages are readily available in libraries.

In embodiments, the electrical property is selected from conductance, resistance, voltage, amperage, capacitance, impedance, inductance, and any combinations thereof. In embodiments, any method is conducted in less than 90 minutes, less than 60 minutes, less than 45 minutes, less than 30 minutes, less than 25 minutes, less than 20 minutes, less than 18 minutes, less than 15 minutes, or less than 12 minutes.

In embodiments, the sample is taken from urine, blood, sweat, mucus, saliva, semen, vaginal secretion, vomit, tears, sebum, pleural fluid, peritoneal fluid, gastric juice, earwax, cerebrospinal fluid, breast milk, endolymph, perilymph, aqueous humor, vitreous humor, biomass and any combinations thereof.

8. Stackable Units—Sample Preparation Automation

In yet another aspect, a diagnostic device for detecting at least one microbe includes a first unit and a second unit; the first unit is stackable into the second unit. The first unit is a diagnostic unit comprising at least one well, the at least one well having electrodes contacting the inside and the outside of the at least one well. The second unit is a reader unit comprising a connector section for the electrodes of the diagnostic unit. In embodiments, the first unit further comprising a sample holder and filter unit, the sample holder and filter unit being in fluidic communication.

In another aspect, a diagnostic device for identifying at least one bacterium in a sample includes a first unit and a second unit; the first unit is stackable into the second unit. The first unit is a diagnostic unit comprising at least one well, the at least one well having electrodes contacting the inside and the outside of the at least one well, a fluidic system comprising of one-way valves and a port for pressurizing the fluidic system. The second unit is a computational reader unit comprising a connector section for the electrodes of the diagnostic unit and connection of at least one micro-pump.

In another aspect, a diagnostic device for identifying at least one bacterium in a sample includes a first unit and a second unit; the first unit is stackable into the second unit. The first unit is a diagnostic unit comprising at least one well, the at least one well having electrodes contacting the inside and the outside of the at least one well. The diagnostic unit can further comprise at least one bacteriophage. The second unit is a computational reader unit comprising a connector section for the electrodes of the diagnostic unit.

In one further aspect, a diagnostic device for determining a count of at least one microbe in a sample comprises a diagnostic unit, which includes at least one well. The at least one well has electrodes contacting the inside and the outside of the at least one well. The diagnostic device further includes a reader unit. The diagnostic unit and the reader unit form a stackable integrated system. The reader unit includes a memory chip which contains correlation data. The correlation data provide a count for microbes taken from data sampled by the reader unit.

In yet one further aspect, a diagnostic device for determining antimicrobial resistance of at least one microbial in a sample includes a first unit and a second unit; the first unit is stackable into the second unit. The first unit is a diagnostic unit comprising one or more wells. The wells have electrodes, which contact the inside and the outside of the at least one well. The diagnostic unit also includes at least one antimicrobial. The second unit is a reader unit, which comprises a connector section for the electrodes of the diagnostic unit.

In embodiments, the diagnostic devices have electrodes including a non-oxidizing material. The non-oxidizing materials can be selected from metals, nonmetals, polymers, composites, resists, resins, carbon nano-tubes, plastics, or any combinations thereof. In a particular embodiment, the diagnostic devices have electrodes that include copper covered with graphene.

9. Automated Sample Preparation

In other embodiments, the diagnostic device further includes a sample inlet, a sample receptacle, a first compartment connected to the sample receptacle, the first compartment containing a first liquid. The diagnostic further includes a filtration chamber containing a waste compartment and a phage compartment; a second compartment connected to the filtration chamber, the second compartment containing a second liquid; and a manifold well unit. The first or the second liquid can be selected from phosphate buffer, sodium bicarbonate, dimethlsulfoxide, NaOH, Methanol or glacial acetic acid, HCL, lactic or hydrochloric acid, aqueous buffer, saline, de-ionized water, broth, or analyte based on Clinical and Laboratory Standards Institute's "Performance Standards for Antimicrobial Susceptibility Testing; Twenty-First Information Supplement", January 2011, Vol 31 No 1. In embodiments, the first or second liquid can be used to reconstitute, dissolve, or prepare agents, such as bacteriophages or antimicrobial compounds, such as antibiotics, antivirals, antifungals, or parasiticides, for mixing the agent with a microbe.

The filtration chamber includes at least one filter comprising a fluorinated polymer. For example, the fluorinated polymer is polyvinylidene fluoride (PVDF). In other embodiments, the filters include a prefilter layer, which can be a cellulose material. For example, the cellulose material can be a cellulose ester. The second and third liquid can be selected from de-ionized water, buffer, saline, broth, analyte, or any combinations thereof. Another embodiment might include additional liquid chambers to accommodate the combined antimicrobials different needs for reconstitution from their dry format. Another embodiment might include additional filters and one-way valves between the chamber where the antimicrobial is reconstituted and the chamber containing the electrodes.

In other embodiments, the diagnostic device further includes a sample inlet, a sample receptacle, a first compartment connected to the sample receptacle, the first compartment containing a first liquid. The diagnostic further includes a filtration chamber containing a waste compartment and a phage compartment; a second compartment connected to the filtration chamber, the second compartment containing a second liquid; and a manifold well unit. The first or the second or third liquid can be selected from phosphate buffer, sodium bicarbonate, dimethlsulfoxide, NaOH, HCL, lactic hydrochloric acid, aqueous buffer, saline, de-ionized water, broth, or analyte or other liquid to reconstitute the dry form of the bacteriophage. The filtration chamber includes at least one filter comprising a fluorinated polymer. For example, the fluorinated polymer is polyvinylidene fluoride (PVDF). In other embodiments, the filters include a prefilter layer, which can be a cellulose material. For example, the cellulose material can be a cellulose ester. The second liquid or third can be selected from de-ionized water, buffer, saline, broth, analyte, or any combinations thereof. Another embodiment might include additional liquid chambers to accommodate the combined bacteriophages different needs for reconstitution from their dry format. Another embodiment might include additional filters and one-way valves between the chamber where the bacteriophage is reconstituted and the chamber containing the electrodes.

In embodiments, the diagnostic has a reader unit that further includes one or more analog to digital converter, one or more memory chip, one or more microprocessor with a computational unit, a system clock, a display processor, and a display. The reader unit can further include one or more micro-pumps to pressurize the diagnostic device and activate the fluidic system.

In yet some embodiments, the diagnostic device has a reader unit that includes a communication device and associated port. In other embodiments, the reader unit includes a port for submitting data. In other embodiments, the reader unit includes a port for receiving data. The port can be a wireless transmitter or a wired communication device.

In embodiments, the diagnostic device includes at least one antimicrobial is selected from aminoglycosides, amphenicols, ansamycins, beta-lactams, lincosamides, macrolides, polypeptide antibiotics, tetracyclines, cycloserine, mupirocin, tuberin, 2,4-diaminopyrimidines, nitrofurans, quinolones, sulfonamides, sulfones, clofoctol, hexedine, methenamine, nitroxoline, taurolidine, and xibernol.

In further embodiments, the at least one antimicrobials is selected from amikacin, azlocillin, carbencillin, cefaclor, cefemandole, cefonicid, cefotaxime, cefoperazone, cefoxitin, ceftizoxime, ceftriaxzone, ciprofloxacin, clindamycin, gatifloxacin, gemifloxacin, gentamicin, kanamycin, linezolid, mecillinam, meropenem, methicillin, metronidazole, mezlocillin, minocyclin, moxifloxacin, nafcillin, netilmycin, oxacillin, penicillin, piperacillin, quinupristin-dalfopristin, sparfloxacin, sulbactam, tazobactam, teicoplanin, tetracyclines, tobramycin, trimethoprim, trospectomycin and vancomycin.

In embodiments, the diagnostic unit has one or more wells with a holding capacity of at least about 1 µL, at least about 10 µL, at least about 20 µL, at least about 50 µL, at least about 100 µL, at least about 200 µL, at least about 500 µL, at least about 1 mL, or at least about 1.5 mL or at least about 2 mL.

In other embodiments, the diagnostic unit has one or more wells with a holding capacity of not greater than about 2 mL, not greater than about 1.5 mL, not greater than about 1 mL, not greater than about 500 µL, not greater than about 200 µL, not greater than about 100 µL, not greater than about 50 µL, or not greater than about 20 µL.

In yet other embodiments, the diagnostic unit has one or more wells with a holding capacity between about 1 µL to about 2 mL, between about 10 µL to about 2 mL, between about 100 µL to about 2 mL, between about 100 µL to about 1.5 mL, between about 100 µL to about 1 mL, between about 500 µL to about 2 mL, between about 500 µL to about 1.5 mL, or between about 500 µL to about 1 mL.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

EXAMPLES

Example 1

Coating of Copper Wire with Graphene

In the embodiment of a single-cell sensor FIG. 8c, an aqueous dispersion of graphene has been prepared by catalytic hydrogenation of humic acid. The humic acid was extracted from leonardite (Agro-Lig) and then catalytically hydrogenated using various catalysts in a Parr reactor at 150° C. The solution is then passed through a strong acid ion exchange column to remove excess cations. The aqueous dispersion of graphene was applied to the copper wire contact points in the sensor with a dropper and allowed to dry. In one embodiment the graphene content might be 0.5% by weight of the aqueous dispersion. In another embodiment the graphene might be 1% by weight. And yet another embodiment the graphene might be 2% by weight.

In further embodiments, alternative techniques are contemplated of applying graphene to either copper or to other materials composing the electrodes.

Example 2

Implementation of Bacteria Identity Determination

Tests were run to show that experiments at room temperature produced the same function over time as experiments held in a water bath at 37 degrees Celsius and this data is not shown here.

In the example implementation, one sensor-well contains the sample at room temperature; the other sensor-well contained T4 bacteriophage specific to *E. coli* B and also at room temperature. In the case of the example implementation the bacteria used were *E. coli* B, the phage used was type T4, the analyte was a supportive culture of LB Broth, but the analyte need not be limited to LB Broth and will be dependent on the types of bacteria being targeted. LB Broth is manufactured by Miller, part number BL 729A. It consists of: Enzymatic Digest of Casein 10 g, Yeast Extract 5 g, Sodium Chloride 10 g, PH is adjusted to 7.3+/−0.2 at 25° C. It could be seen that the resistance of the analyte first lowered during the first part of the phage attack and then returned to starting point at about 201 seconds as the bacteria reabsorbed the potassium ions.

Example 3

Implementation of Antimicrobial Determination

An overnight bacterial culture of *E. coli* B with a concentration of around $10^9$ cells which had attained room temperature were diluted using LB Broth which had also attained room temperature to a final concentration of $10^3$ cells. 0.9 ml of this solution was then placed into one sensor well which was connected to lead #1 of a reader unit. An additional 0.9 ml of the bacteria was placed into a second sensor well which was connected to lead#2 of a reader unit. Data were collected on these solutions for around 4 minutes before the addition of either antibiotic or $diH_2O$. At second 263, 0.1 mL of Sulfamethoxazole stock solution which had attained room temperature was added to the first sensor well, and at second 283, room temperature $diH_2O$ was added to the second sensor well and data collection was continued. All sensors wells were rinsed with 70% ethanol and the rinsed 10 times with $diH_2O$ before the following test.

An overnight bacterial culture of *E. coli* B with a concentration of around $10^9$ cells that had attained room temperature were diluted to a final concentration of $10^3$ cells. 0.9 ml of this solution was then placed into a first sensor well which was connected to lead #1 of a reader unit. An additional 0.9 ml of the bacteria was placed into a second sensor well which was connected to lead#2 of a reader unit. Data were collected on these solutions for around 1 minute before the addition of either antibiotic or $diH_2O$. At second 63, 0.1 ml of Trimethoprin stock solution which had attained room temperature was added to the first sensor well, and at second 278 room temperature $diH_2O$ was added to the second sensor well and data collection was continued for some time. All sensors were rinsed with 70% ethanol and the rinsed 10 times with $diH_2O$ before the following test.

A two hour *E. coli* B bacteria culture with a concentration of around $10^7$ cells that had attained room temperature were diluted in LB Broth to a final concentration of $10^3$ cells. 0.9 mL of this solution was then placed into sensor well which was connected to lead #1 of the reader unit. An additional 0.9 mL of the bacteria was placed into a second sensor well which was connected to lead #2 of the reader unit. Data was collected on these solutions which were left at room temperature for around 10 minutes before the addition of either antimicrobial or $diH_2O$. At second 679, 0.1 mL of Polymyxin stock solution which had attained room temperature was added to a sensor well and at second 702, $diH_2O$ was added to another sensor well and data was collected for some time. All sensors were rinsed with 70% ethanol and the rinsed 10 times with diH2O before the following test.

A *E. coli* B bacteria culture was grown for around 2 hours and thirty minutes with a concentration of around $10^7$ cells and which had attained room temperature were further diluted in LB Broth that had attained room temperature to a final concentration of $10^3$ cells. Then 0.9 mL of this solution was then placed into a sensor well which was connected to lead #1 of the reader unit. An additional 0.9 ml of the bacteria was placed into another sensor well which was connected to lead #2 of the reader unit. Data was collected on these solutions for around 10 minutes and left to grow at room temperature before the addition of either antibiotic or $diH_2O$. At second 665, 0.1 mL of the Azithromycin which had attained room temperature was added to the sensor well, and at second 676, 0.1 mL of $diH_2O$ was added to the other sensor well. All sensors were rinsed with 70% ethanol and the rinsed 10 times with $diH_2O$ before the following test.

Example 4

Bacteria Viability Determination

Bacteria viability test was implemented by measuring resistance of samples containing various concentrations of colony forming units (CFU) of *E. Coli* B which had attained room temperature was suspended in LB Broth which had also attained room temperature. Samples have the following concentration: $10^2$ CFU/mL, $10^4$ CFU/mL, $10^5$ CFU/mL, $10^6$ CFU/mL, $10^7$ CFU/mL and $10^9$ CFU/mL. The bacteria were left to grow at room temperature for 111 seconds and the resistance decreased as a function of time. The test was run at room temperature after the LB Broth and bacteria had also reached room temperature.

Bacteria viability test was also implemented in artificial urine by measuring resistance of samples containing various concentrations of colony forming units (CFU) of *E. Coli* B. Samples have the following concentration: $10^2$ CFU/mL, $10^4$ CFU/mL, $10^5$ CFU/mL, $10^6$ CFU/mL, $10^7$ CFU/mL and $10^9$ CFU/mL. The bacteria were left to grow for 111 seconds at room temperature and the resistance decreased as a function of time. The sensors detect the growth of the bacteria indicated by a decrease in resistance of the analyte. The test was run at room temperature after the artificial urine and bacteria had also reached room temperature. Artificial Urine was prepared with ingredients disclosed in Table 1. Part A and Part B were prepared separately, ingredients were combined from each part according the amount in Table 1. The pH was adjusted to 5.8. The solution was sterilized by filtration. Part B was added aseptically to Part A to give 2 L of artificial urine. The artificial urine was stored at 4 degree Celsius and could last for 1-1.5 weeks

TABLE 1

Artificial Urine Recipe

| Ingredient | Amount | | Notes |
|---|---|---|---|
| Part A | | | |
| $H_2O$ | 1.8 | L | |
| $MgCL_2*6H_2O$ | 1.302 | g | |
| NaCl | 9.2 | g | |
| $Na_2SO_4$ | 4.6 | g | |
| Na citrate | 1.302 | g | |
| Na oxalate | 0.004 | g | |
| $KH_2PO_4$ (monobasic) | 5.6 | g | |
| KCL | 3.2 | g | |
| TSB (Tryptic Soy Broth) | 20.0 | g | |
| Part B | | | |
| $H_2O$ | 200 | mL | |
| $NH_4CL$ | 2.0 | g | |

TABLE 1-continued

Artificial Urine Recipe

| Ingredient | Amount | Notes |
|---|---|---|
| $CaCl_2 \cdot 2H_2O$ | 1.302 g | |
| Urea | 50.0 g | |
| Creatinine | 2.2 g | |

Example 5

Implementation of Reader

FIG. 8 discloses an implementation of a reader unit system. A sample well having electrodes is attached to Leads that are connected to sensors. The reader unit collects data over time from which signature plots are generated.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

What is claimed is:

1. A method of determining antimicrobial activity of an agent, comprising:
   providing a well, the well containing at least one antimicrobial agent, the well further including at least two electrodes;
   adding a sample of at least one microbe into the well;
   pulsing a voltage between the at least two electrodes, wherein the voltage is ranging from about 0.0005 V to about 2.0 V;
   sampling an electrical property during the pulsing; and
   recording the electrical property.

2. The method according to claim 1, wherein the method further comprises:
   repeating the pulsing, the sampling and the recording, and plotting the recordings versus time to form a signature.

3. The method according to claim 1, wherein the at least one microbe is selected from bacteria, fungi, viruses, or nematodes.

4. The method according to claim 1, wherein the at least one antimicrobial agent is selected from bacteriophages, mycoviruses, virophages, nematophages, antibiotics, antimicrobials, antivirals, antifungals, or parasiticides.

5. The method according to claim 1, the method further comprising measuring a temperature or a pH inside the well.

6. The method according claim 1, wherein the pulsing includes an on-period and an off-period, the sum of the on-period and the off-period comprising a sample-period.

7. The method according to claim 6, wherein the sampling of the electrical property occurs during the sample-period.

8. The method according claim 6, wherein the sampling of the electrical property is at least about 0.5 milliseconds.

9. The method according to claim 1, wherein the determining of antimicrobial activity is between about 15 seconds and about 60 minutes.

10. A method of identifying at least one microbe, comprising:
    taking a sample containing the at least one microbe;
    isolating the at least one microbe from the sample;
    dividing the at least one microbe into a at least one wells, each well containing at least one antimicrobial agent, each well including at least two electrodes;
    pulsing a voltage between the at least two electrodes, wherein the voltage is ranging from about 0.0005 V to about 2.0 V;
    sampling an electrical property during the pulsing; and
    recording the electrical property for a sample-duration as a function of time.

11. The method according to claim 10, wherein the isolating further comprises:
    filtering the sample to separate the at least one microbe from the sample, and
    immersing the at least one microbe in an analyte.

* * * * *